(12) United States Patent
Basheer et al.

(10) Patent No.: US 11,385,183 B2
(45) Date of Patent: Jul. 12, 2022

(54) METHOD FOR DETECTING COPPER(II) IONS USING A HYDRAZONE-BASED COLORIMETRIC SENSOR

(71) Applicant: King Fahd University of Petroleum and Minerals, Dhahran (SA)

(72) Inventors: Chanbasha Basheer, Dhahran (SA); Abdulaziz A. Al-Saadi, Dhahran (SA); Ismail Abdulazeez, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 376 days.

(21) Appl. No.: 16/596,896

(22) Filed: Oct. 9, 2019

(65) Prior Publication Data

US 2021/0109027 A1    Apr. 15, 2021

(51) Int. Cl.
*G01N 21/78* (2006.01)
*C07C 251/86* (2006.01)

(52) U.S. Cl.
CPC .......... *G01N 21/78* (2013.01); *C07C 251/86* (2013.01)

(58) Field of Classification Search
CPC .............. G01N 21/78; C07C 251/86
See application file for complete search history.

(56) References Cited

U.S. PATENT DOCUMENTS 5,620,658 A * 4/1997 Jaunakais .............. G01N 31/22
    422/401
5,766,478 A * 6/1998 Smith .................. B01D 61/145
    210/638

FOREIGN PATENT DOCUMENTS

CN    102816086 A    12/2012
CN    107759489 A    3/2018
(Continued)

OTHER PUBLICATIONS

A selective detection approach for copper ions using a hydrazone based colorimetric sensor: spectroscopic and DFT study. Ismail Abdulazeez, Chanbasha Basheer, Abdulaziz A. Al-Saadi RSC Adv., 2018, 8, 39983-39991 (Year: 2018).*

(Continued)

*Primary Examiner* — Brian R Gordon
*Assistant Examiner* — Dwan A Gerido
(74) *Attorney, Agent, or Firm* — Oblon, McClelland, Maier & Neustadt, L.L.P.

(57) ABSTRACT

Cu(II) detection in the presence of main group heavy metal ions and d-, f- and g-element interferents relies on a colorimetric chelating complex between 3-hydroxy-5-nitrobenzaldehyde-4-hydroxybenzoylhydrazone (3-HNHBH) and Cu(II). Derivatives and entrapped forms of the probe were aligned with the methods of analysis, featuring spectrophotometric, reflectometric, lateral flow, microfluidic, lab-on-paper, positional array, dynamic array, flow cytometry and tandem stage devices. A remotely operating software capable of DFT calculations predicted the observed detection limit of 0.34 µg $L^{-1}$ (<5 nM) as well as high selectivity towards copper ions in the presence of competing Zn+2 and Ni+2. The probe was readily regenerated against metal complexation by using a 0.5 M HCl solution, indicating its feasibility to be a re-usable sensor for the convenient detection of copper ions in water-organic media. The influence of metal interference, pH and solvents on the selectivity and regeneration of the ligand was incorporated in an algorithm providing decision support to the analyst via smartphone, laptop and other multimedia.

6 Claims, 13 Drawing Sheets

Keto form

Enol form

(56) References Cited

FOREIGN PATENT DOCUMENTS

| CN | 108358814 A | 8/2018 |
|----|-------------|--------|
| CN | 106220531 B | 9/2018 |

OTHER PUBLICATIONS

Printed Disposable Colorimetric Array for Metal Ion Discrimination. M. Ariza-Avidad, A. Salinas-Castillo, M.P. Cuellar, M. Agudo-Acemel, M.C. Pegalajar, L.F. Capitan-Vallvey Anal. Chem. 2014, 86, 8634-8641 (Year: 2014).*

Sangeetha, et al. ; Synthesis, structure and properties of a dicopper(II) complex ; Polyhedron, vol. 18, Issue 10 ; pp. 1425-1429 ; Mar. 26, 1999 ; Abstract Only ; 2 Pages.

Gunnlaugsson, et al. ; Highly Selective Colorimetric Naked-Eye Cu(II) Detection Using an Azobenzene Chemosensor ; ASCPublications ; Organic Letters, 6, 10 ; pp. 1557-1560 ; 2004 ; Abstract Only ; 2 Pages.

Ganjali, et al. ; Design and construction of a novel optical sensor for determination of trace amounts of dysprosium ion ; Sensors and Actuators B: Chemical, vol. 143, Issue 1 ; pp. 233-238 ; Dec. 4, 2009 ; Abstract Only ; 2 Pages.

Wang, et al. ; A colorimetric chemosensor for Cu21 ion detection based on an iridium(III) complex ; Scientific Reports ; Oct. 28, 2014 ; 7 Pages.

* cited by examiner

Keto form          Enol form

METHOD FOR DETECTING COPPER(II) IONS USING A HYDRAZONE-BASED COLORIMETRIC SENSOR

STATEMENT OF PRIOR DISCLOSURE BY INVENTORS

Aspects of the present disclosure were described by the inventors in "A selective detection approach for copper(II) ions using a hydrazone-based colorimetric sensor: spectroscopic and DFT study," RSC Adv., 2018, 8, 39983, which published online on Nov. 30, 2018.

STATEMENT OF ACKNOWLEDGEMENT

Inventors gratefully acknowledge the support of this work by King Fahd University of Petroleum and Minerals (KFUPM).

BACKGROUND

Field of the Invention

The present disclosure relates to methods and systems for complexometric colorimetric detection of transition metal ions in the presence of competing species.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or implicitly admitted as prior art against the present disclosure.

Copper is an essential element that is required in the human body with a delicate balance between deficiency, which could result in ailments such as anemia, and excess, which could cause di□erent types of diseases, such as hypoglycemia and dyslexia. See Aksuner, N. E. Henden, I. Yilmaz and A. Cukurovali, Dyes Pigm., 2009, 83, 211-217). Copper is necessary for the catalytic activity of several physiologically important enzymes. See D. Strausak, J. F. B. Mercer, H. H. Dieter, W. Stremmel and G. Multhaup, Brain Res. Bull., 2001, 55, 175-185. Hereditary copper metabolism disorders and neurodegenerative ailments have been associated with dysfunctional copper-binding proteins and the disruption of cellular homeostasis. See D. R. Brown and H. Kozlowski, Dalton Trans., 2004, 1907-1917, DOI: 10.1039/b401985g; D. J. Waggoner, T. B. Bartnikas and J. D. Gitlin, Neurobiol. Dis., 1999, 6, 221-230; and H.-G. Li, Z.-Y. Yang and D.-D. Qin, Inorg. Chem. Commun., 2009, 12, 494-497.

The common use of copper domestically and industrially has resulted in a widespread exposure and pollution that warrant the development of a means to monitor its level in the environment, water and food. See, Aksuner et al.; V. K. Gupta, A. K. Jain, G. Maheshwari, H. Lang and Z. Ishtaiwi, Sens. Actuators, B, 2006, 117, 99-106; X. Q. Chen, M. J. Jou, H. Lee, S. Z. Kou, J. Lim, S. W. Nam, S. Park, K. M. Kim and J. Yoon, Sens. Actuators, B, 2009, 137, 597-602.

Conventional techniques for the detection of copper and other heavy metal ions include the use of fluorescent probes, atomic absorption spectrometry, inductively coupled plasma-mass spectrometry and electrochemical assays. See L. Sen, T. Jingqi, W. Lei, Z. Yingwei, Q. Xiaoyun, L. Yonglan, A. M. Abdullah, A.-Y. O. Abdulrahman and S. Xuping, Adv. Mater., 2012, 24, 2037-2041; S. L. C. Ferreira, M. A. Bezerra, A. S. Santos, W. N. L. dos Santos, C. G. Novaes, O. M. C. de Oliveira, M. L. Oliveira and R. L. Garcia, TrAC, Trends Anal. Chem., 2018, 100, 1-6; L. Fernandez-López, B. Gómez-Nieto, M. J. Gismera, M. T. Sevilla and J. R. Procopio, Spectrochim. Acta, Part B, 2018, 147, 21-27; I. D. la Calle, P. Pérez-Rodríiguez, D. Soto-Gómez and J. E. López-Periago, Microchem. J., 2017, 133, 293-301; L. Tian, J. Qi, K. Qian, O. Oderinde, Q. Liu, C. Yao, W. Song and Y. Wang, J. Electroanal. Chem., 2018, 812, 1-9; A. Ismail, A. Kawde, O. Muraza, M. A. Sanhoob and A. R. Al-Betar, Microporous Mesoporous Mater., 2016, 225, 164-173; and A. Kawde, A. Ismail, A. R. Al-Betar and O. Muraza, Microporous Mesoporous Mater., 2017, 243, 1-8. While these analytical methods show excellent sensitivity, accuracy and selectivity, they lack the convenience in implementation, require specialized instrumentations and need tedious sample pre-treatment before the course of analysis.

Hence, recently attention have been turned to the colorimetry-based detection approach to test for the presence of toxic metal ion traces in aqueous media. See Y. Ping, Z. Chen, Q. Ding, Q. Zheng, Y. Lin and Y. Peng, Tetrahedron, 2017, 73, 594-603; and F.-U. Rahman, S.-B. Yu, S. K. Khalil, Y. P. Wu, S. Koppireddi, Z.-T. Li, H. Wang and D.-W. Zhang, Sens. Actuators, B, 2018, 263, 594-604. Such an approach is considered less-labor intensive compared to conventional techniques, o□ers high sensitivity and selectivity, in addition to cost e□ectiveness towards the detection of metal ions. One main advantage of colorimetric detections is that it is less capital-intensive and hence exhibits the potential to be developed into simple test kits for on-site and regular inspections. See R. Sheng, P. Wang, Y. Gao, Y. Wu, W. Liu, J. Ma, H. Li and S. Wu, Org. Lett., 2008, 10, 5015-5018.

Several studies have been reported on the colorimetric detection of copper ions in various media. Jo et al. reported the synthesis of a multifunctional chemosensor for the detection of cyanide and copper ions. See T. G. Jo, Y. J. Na, J. J. Lee, M. M. Lee, S. Y. Lee and C. Kim, Sens. Actuators, B, 2015, 211, 498-506. Moreover, a naphthol-based chemosensor for sequential detection of copper and cyanide ions has been reported by Park et al. See G. J. Park, I. H. Hwang, E. J. Song, H. Kim and C. Kim, Tetrahedron, 2014, 70, 2822-2828. Other functional materials already reported for the detection and removal of toxic metal ions at optimum conditions include, hydroxynaphthalene-based, quinazoline-based, silica-based, hydrazine-based, salicylidene-based and aroylhydrazone-based compounds. See S. A. Lee, J. J. Lee, J. W. Shin, K. S. Min and C. Kim, Dyes Pigm., 2015, 116, 131-138; M. R. Awual, T. Yaita and Y. Okamoto, Sens. Actuators, B, 2014, 203, 71-80; A. Mohammadi and S. Yaghoubi, Sens. Actuators, B, 2017, 241, 1069-1075; M. R. Awual, M. Ismael, T. Yaita, S. A. El-Safty, H. Shiwaku, Y. Okamoto and S. Suzuki, Chem. Eng. J., 2013, 222, 67-76; M. R. Awual and M. M. Hasan, Sens. Actuators, B, 2015, 206, 692-700; M. R. Awual, T. Yaita, S. A. El-Safty, H. Shiwaku, S. Suzuki and Y. Okamoto, Chem. Eng. J., 2013, 221, 322-330; M. R. Awual, I. M. M. Rahman, T. Yaita, M. A. Khaleque and M. Ferdows, Chem. Eng. J., 2014, 236, 100-109; M. R. Awual, Chem. Eng. J., 2015, 266, 368-375; M. R. Awual, M. M. Hasan, M. A. Khaleque and M. C. Sheikh, Chem. Eng. J., 2016, 288, 368-376; M. R. Awual, Chem. Eng. J., 2017, 307, 85-94; M. R. Awual, J. Ind. Eng. Chem., 2014, 20, 3493-3501; and M. Pannipara, A. G. Al-Sehemi, M. Assiri and A. Kalam, Opt. Mater., 2018, 79, 255-258.

One important conclusion drawn out of these studies was that aroylhydrazone-based sensors could be promising candidates due to the ease of synthesis, fast-response, reusability, and tunable electronic and steric properties along with their chelating ability. See S. Naskar, S. Naskar, S. Mondal, P. K. Majhi, M. G. B. Drew and S. K. Chattopadhyay, *Inorg. Chim. Acta*, 2011, 371, 100-106; and A.-M. Stadler and J. Harrowfield, *Inorg. Chim. Acta*, 2009, 362, 4298-4314.

Aroylhydrazone-based sensors were as well patented by other groups. CN108358814A and a similar CN107759489A discloses benzoyl hydrazine derivative used in fluorescence method on metal ions, and particularly relates to a benzoyl hydrazine derivative p which identifies and detects two different metal ions Mg(II) and Al(III) separately in different pH conditions. The method of this disclosure relies on fluorescence and is not optimized for Cu (II) detection. CN108358814A discloses AIE (aggregation-induced emission) fluorescent probe based on salicylaldehyde hydrazone derivative as well as preparation method and application of AIE fluorescent probe for copper ions in an aqueous solution. In operation, the probe changes from orange fluorescence to zero, has colorimetric fluorescence quenching effect, the copper ions can be detected visually; the probe is particularly applicable to detection of the copper ions in cells. The compound structurally differs from the inventive formula and depends on aggregation-induced emission, while the inventive method is purely colorimetric. T. Gunnlaugsson, J. P. Leonard and N. S. Murray in *Organic letters*. 2004, 6(10), 1557-60, discloses colorimetric azobenzene based chemosensors 1 and 2 designed for detection of transition-metal ions such as Cu (II) under physiological pH conditions. The internal charge transfer (ICT) sensors are highly colored, absorbing in the green. For 1, the Cu (II) recognition gives rise to red-to-yellow color changes that are directly visible and reversible upon addition of EDTA. The sensor of Gunnlaugsson et al. is distinct from the inventive compound structurally and spectrally. CN102816086A discloses salicylidenehydrazine receptor compound used as selective Cu(II) colorimetric identification reagent, obtained by condensing salicylaldehyde and hydrazine hydrate. While the spectrum of the compound is analogous to the inventive spectrum, the disclosure does not specify the detection limits of Cu(II), the identities of the competing ions and specific enabling conditions of analysis. US 2006/0252798 A1 to Richardson et al. discloses specific complexation of Cu (II) by hydroxybenzoylhydrozones. The generic and specific structures of the invention differ from the claimed in this application, and the method of Richardson's invention is a medical treatment, not a colorimetric analysis in the presence of iso-valent interfering species. CN104529887A discloses a pyridyl-hydrazone compound used for selective colorimetric recognition of copper ions. Lower limit of copper ions detected by naked eye using the compound can reach 2 micromoles (400-fold less sensitive than the inventive threshold). At the same time, the chemical structure of the probe in this method substantially differs from the inventive. The reference does not mention iso-valent competing species and does not define the enabling conditions for analytical resolution. Finally, WO18162396A1 discloses cross-linked aryl-hydrazone copolymers in the form of dense or porous membranes (films) and their application as colorimetric sensors of divalent metals and/or oxidizing anions in aqueous media, such as—for example—in drinking and industrial water, and in food products. Yet, the claimed subject structure is distinct from the referenced in WO18162396A1.

Accordingly, it is one object of the present disclosure to provide a system, method and facility for selective analysis of Cu(II) in the presence of interferents, adapted for colorimetric and visual detection. Especially advantageous would have been a ligand forming a stable 5-member ring with the chelated transition metal and enabling a specific detection at a low threshold and at a high ratio of the interferents to the target ion. Even more advantageous would have been such detection conducted by naked eye using a small portable kit. Colorimetric sensing ability towards metal ions, including zinc (II), nickel (II) and copper (II), has been evaluated and unexpectedly, the inventors encountered favorable functional and economic properties of 3-hydroxy-5-nitrobenzaldehyde-4-hydroxybenzoylhydrazone (3-HNHBH).

SUMMARY OF THE INVENTION

According to a first aspect, the present disclosure relates to a method and system for selective complexometric colorimetric detection of Cu(II) in the presence of interfering iso-valent species using a compound of structure (I):

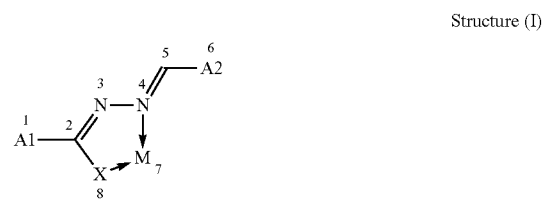

Structure (I)

wherein A1 is at least a double substituted aryl or heteroaryl, wherein the first substituent is carbon 2, the second substituent is OH, NH2, SH or halogen group, wherein the remaining substituents are H, optionally substituted linear alkyl, branched alkyl, cycloalkyl, vinyl, diene, dienophile, alkyne or a polymer.

wherein X is OH, =O, NH2, =N—H, —N=N=H groups;

wherein A2 is at least a triple substituted aryl or heteroaryl; wherein the first substituent is carbon 5, the second substituent is NO2, COOH, COOR, COR, SO3, wherein R is an optionally substituted linear or branched alkyl or cycloalkyl, the third substituent is OH, NH2, —N=NH2, SH, and the remaining substituents are H, optionally substituted linear alkyl, branched alkyl, cycloalkyl, vinyl, allyl, diene, dienophile, alkyne or a polymer;

wherein M is Cu(II).

According to a second aspect, the present disclosure relates to a Structure (II),

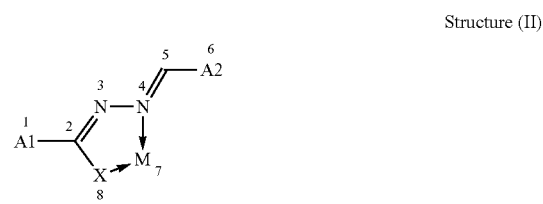

Structure (II)

wherein:

[A1] of Structure (II) is a double substituted phenyl, wherein the first substituent is carbon 2 in a para-position to the second substituent, the second substituent is OH group, wherein the remaining substituents are independently H or a single optionally substituted vinyl, alkyne, diene, dienophile or a polymer group;

wherein the polymer is a radical polymerization network, a grafted solid support, a microsphere, a dendrimer, a gel, a matrix without limitation;

wherein X is OH or =O groups as a part of tautomeric equilibrium, wherein A2 is at least a triple substituted phenyl ring; wherein the first substituent is carbon 5 in a para position to the second substituent and meta position to the third substituent, the second substituent is NO2, the third substituent is OH, and the remaining substituents are H or a single optionally substituted vinyl, alkyne, diene, dienophile or polymer group;

wherein the polymer is a radical polymerization network, a grafted solid support, a microsphere, a dendrimer, a gel, a matrix without limitation;

wherein M is Cu(II).

According to a third aspect, the present disclosure relates to metal complexes of 3-hydroxy-5-nitrobenzaldehyde-4-hydroxybenzoylhydrazone (3-HNHBH) ligand:

multistage sequential separations utilizing affinity/ion-exchange pre-concentration steps.

According to an eighth aspect, the present disclosure relates to stand off reflectometric measurements collected across extensive areas or under conditions when a toxic atmosphere or other risks to the operator are present.

According to the ninth aspect, the present disclosure related to computerized decision-assistance for all analytical steps and analysis of the results.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

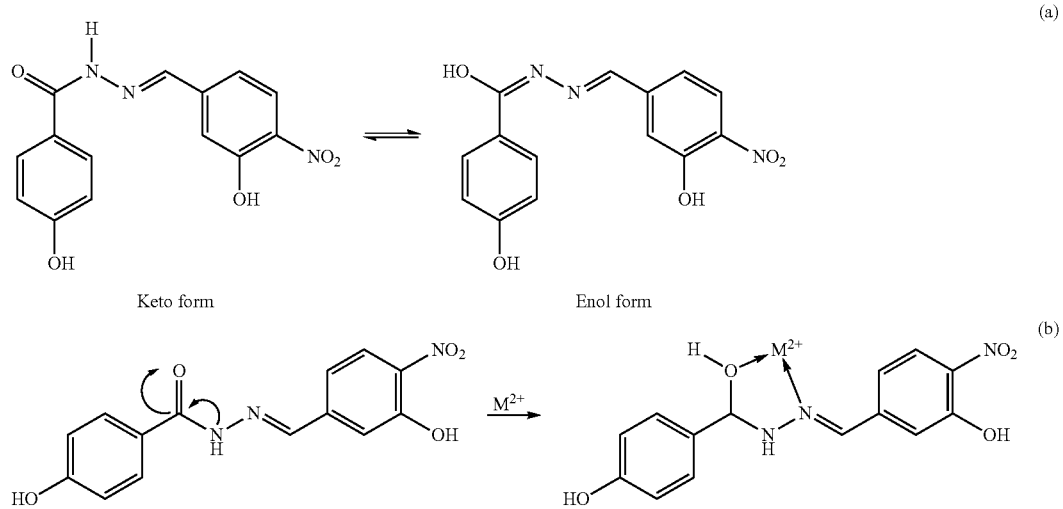

According to a fourth aspect, the present disclosure relates to the method of use of the embodiments of Structure (I) and Structure (II) for colorimetric detection of Cu(II) in the presence of Zn(II) and/or Ni(II), at very low detection threshold, at high dynamic range of concentrations and at high ratios of interfering ions to the target.

According to a fifth aspect, the present disclosure relates to a computational method for predicting of optimal differential spectra of the target ions in the presence of defined interferents, acidity and polarity of the solvent.

According to a sixth aspect, the present disclosure relates to an environment monitoring kit with instructions for measuring the presence of Cu(II) in drinking water, ponds, rivers, wells, ground waters, industrial spills, fracking fluids, recycles.

Figure 3A:
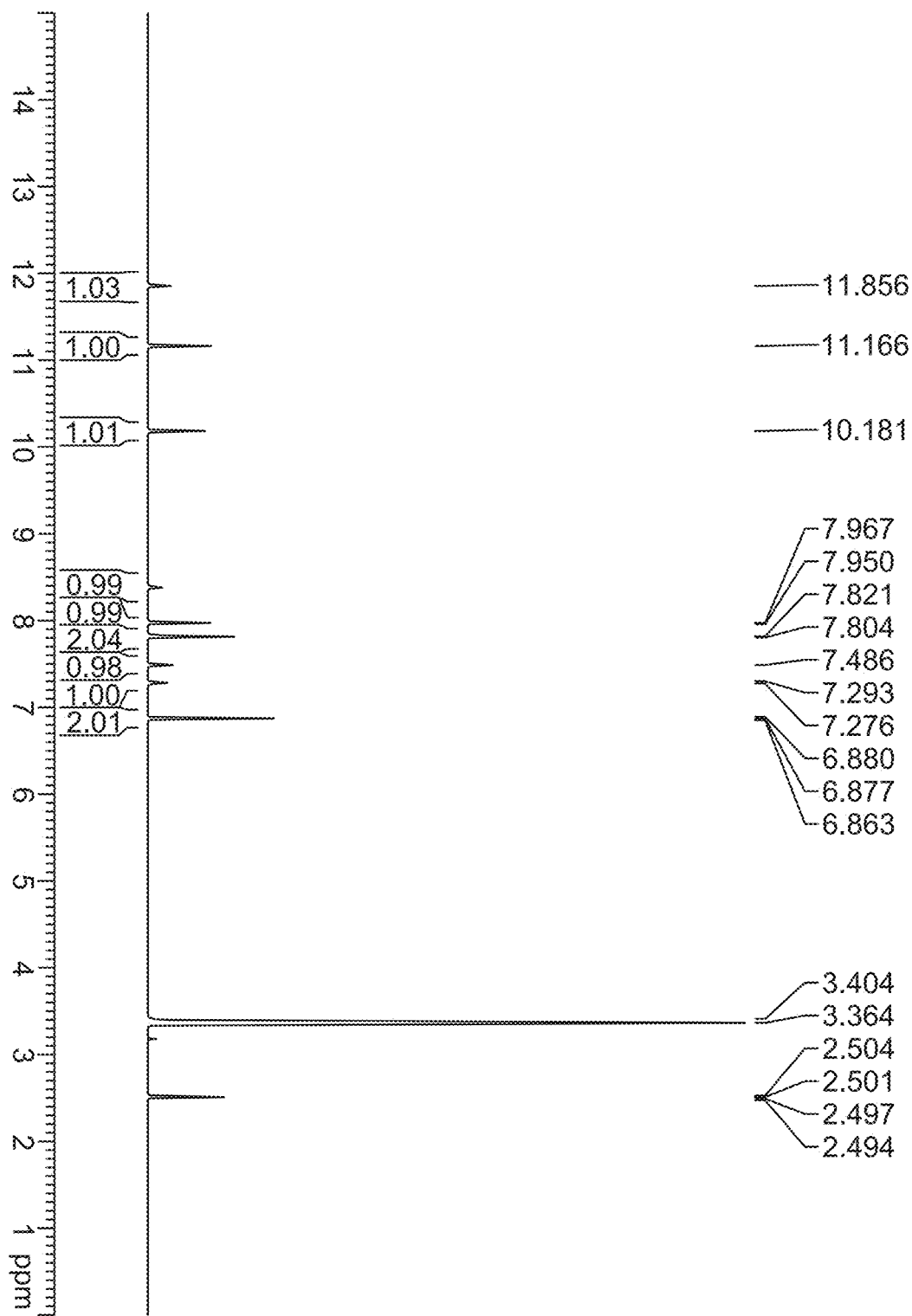

According to a seventh aspect, the present disclosure relates to the use of immobilized probe incorporated covalently in a matrix, grafted on a polymer or non-covalently absorbed on hydrophobic-hydrophilic supports, and used in lateral flow devices, colorimetric arrays, cPMD devices and FIG. 3A is a graph illustrating the $^1$H NMR spectra in DMSO-d6 of 3-HNHBH ligand (a) before complexation with Cu(ii) ions.

Figure 3B:
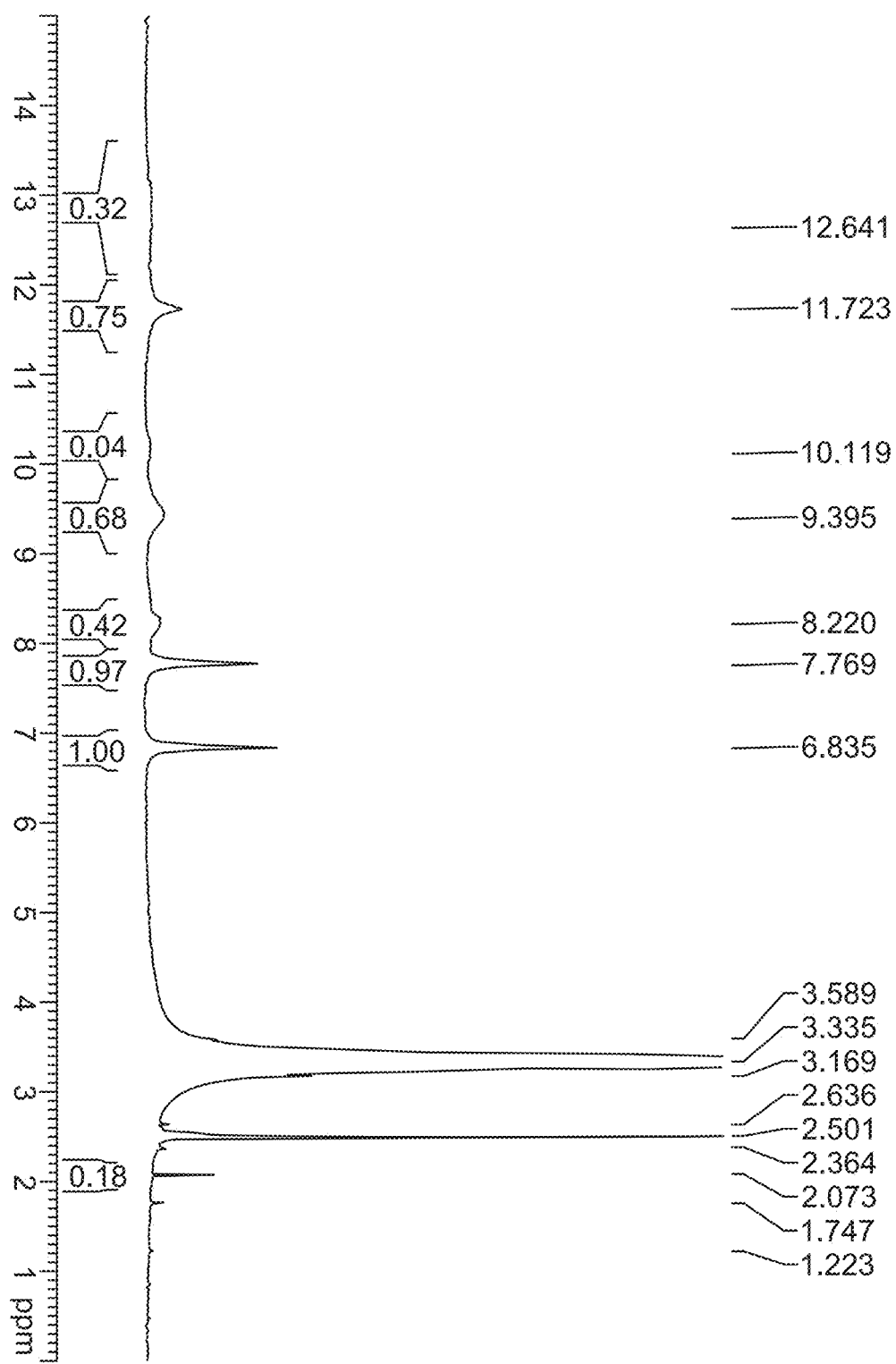

FIG. 3B is a graph illustrating the $^1$H NMR spectra in DMSO-d6 of 3-HNHBH ligand after complexation with Cu(ii) ions.

Figure 4:
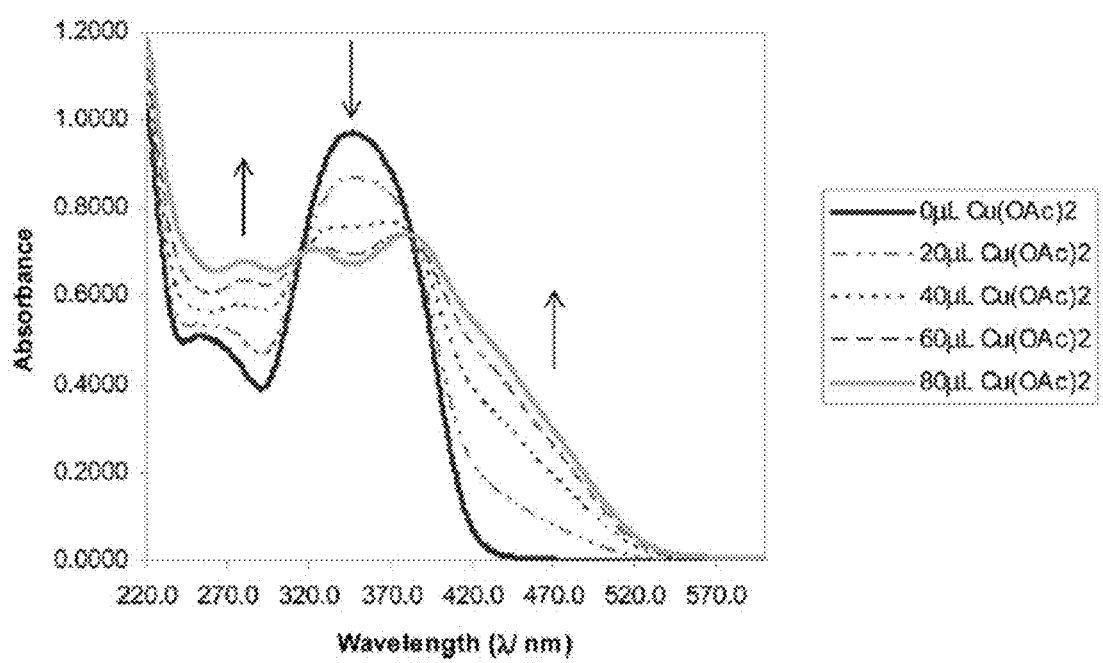

FIG. 4 is a graph illustrating the absorbance vs. wavelength (λ/nm) of ligand/THF with $Cu(OAc)_2$. Some spectra omitted for clarity.

Figure 5A:
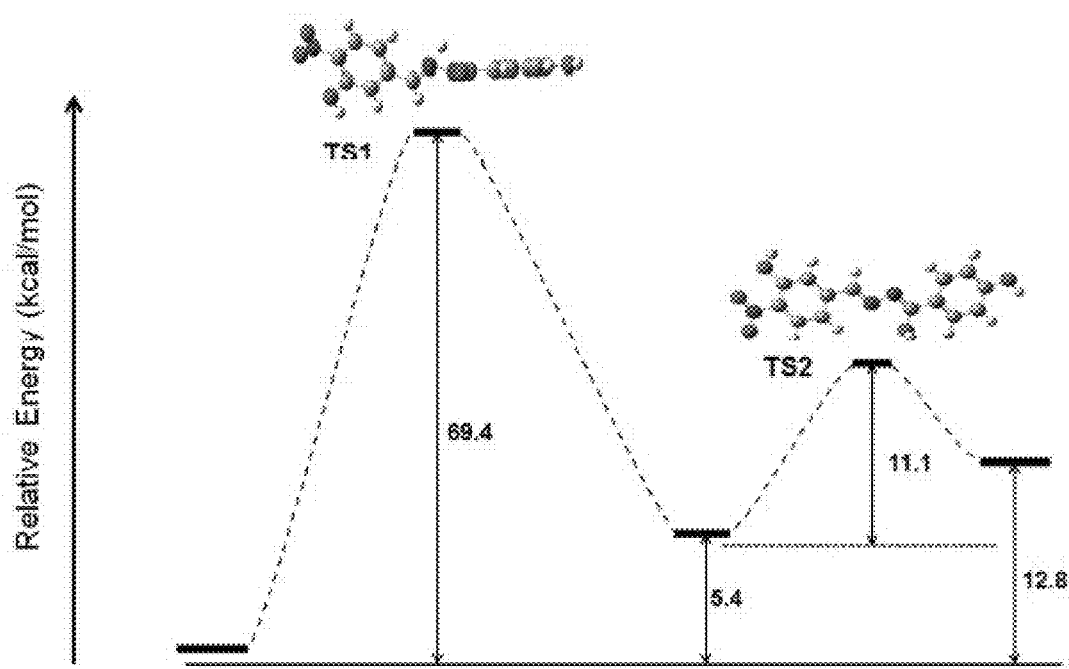
Figure 5B:
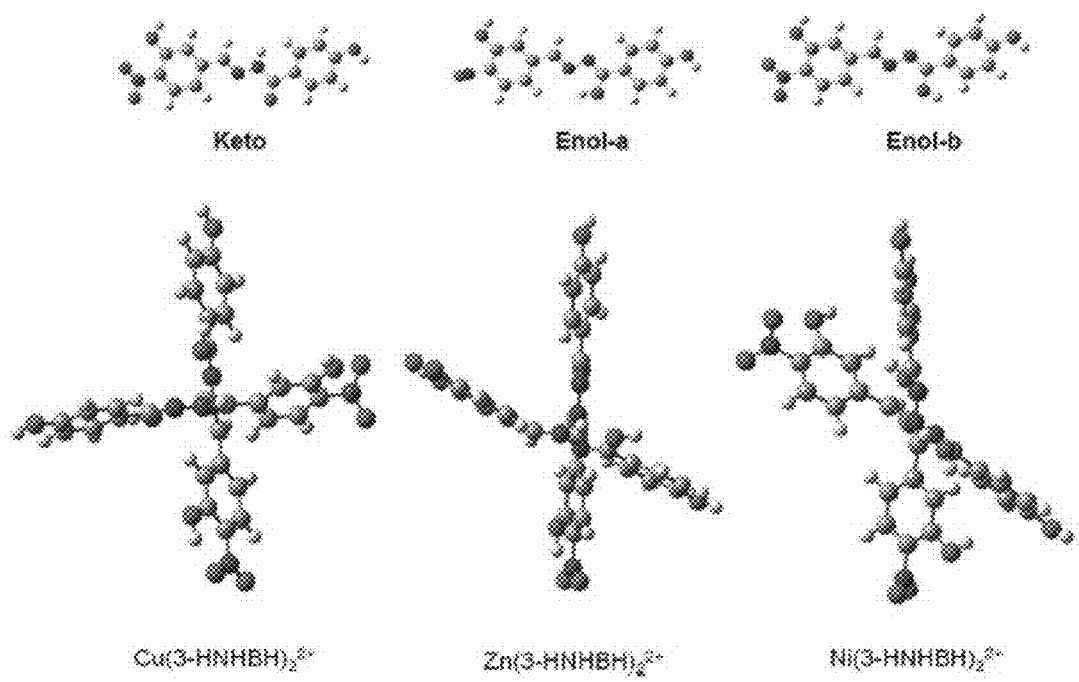

FIGS. 5A-5B illustrate (a) Suggested step-wise keto-enol tautomerization of 3-HNHBH ligand prior to complexation to the metal ion center, and (b) optimized metal-ligand complexes of 3-HNHBH with Ni(ii), Cu(ii) and Zn(ii) ions, calculated at the B3LYP/6-311+G(d) level of theory.

Figure 6:
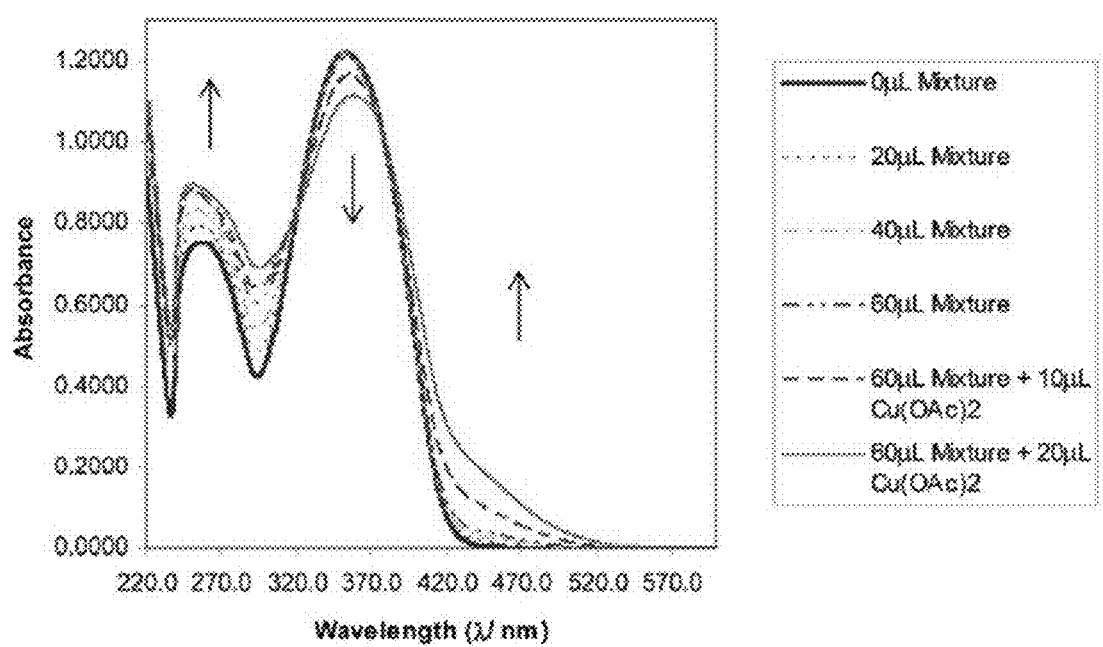
Figure 7A:
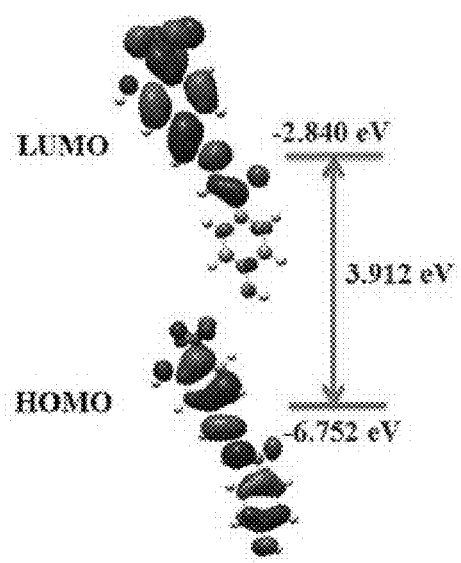
Figure 7B:
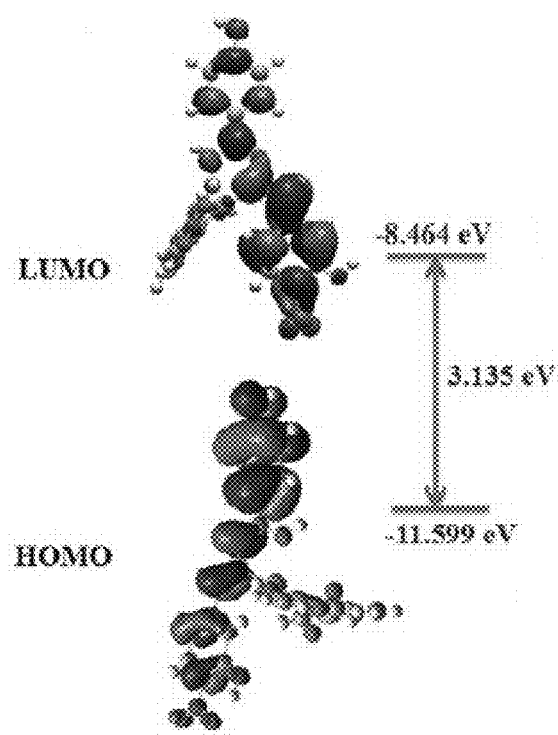
Figure 7C:
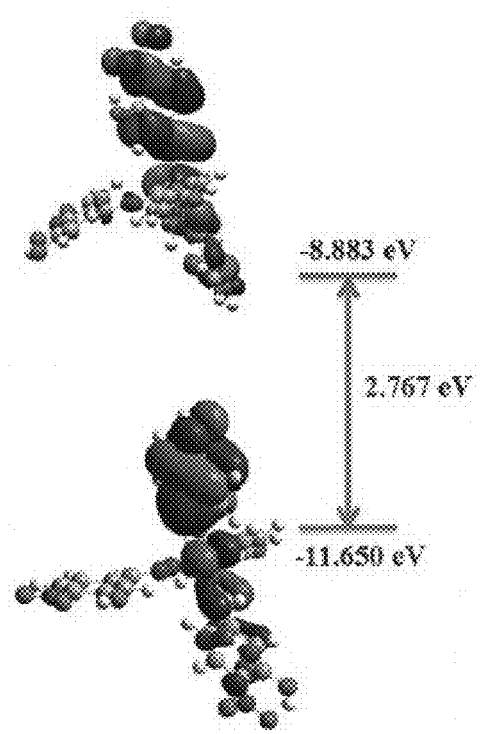
Figure 7D:
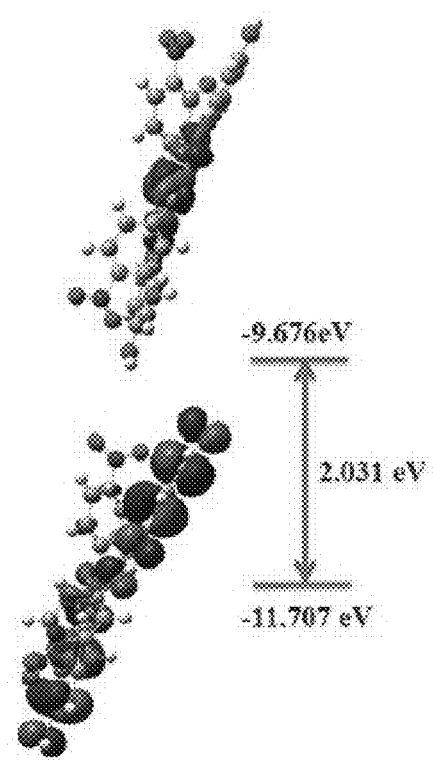

FIG. 6 is a graph illustrating the absorbance vs. wavelength (λ/nm) of ligand/THF with metal interference solutions in THF. Some spectra omitted for clarity.

FIGS. 7A-7D illustrate the calculated frontier molecular orbitals of 3-HNHBH and the corresponding HOMO and LUMO orbital energies (a) before, and after complexation with (b) Cu(ii), (c) Zn(ii) and (d) Ni(ii) metal ions.

DETAILED DESCRIPTION OF THE INVENTION

The foregoing paragraphs have been provided by way of general introduction and are not intended to limit the scope of the following claims. The described embodiments, together with further advantages, will be best understood by reference to the following detailed description taken in conjunction with the accompanying drawings. The present disclosure will be better understood with reference to the following definitions.

As used herein, the words "a" and "an" and the like carry the meaning of "one or more". Additionally, within the description of this disclosure, where a numerical limit or range is stated, the endpoints are included unless stated otherwise. Also, all values and subranges within a numerical limit or range are specifically included as if explicitly written out.

As used herein, the terms "optional" or "optionally" means that the subsequently described event(s) can or cannot occur or the subsequently described component(s) may or may not be present (e.g. 0 wt %).

The term "comprising" is considered an open-ended term synonymous with terms such as including, containing or having and is used herein to describe aspects of the invention which may include additional reaction steps, components, functionality and/or structure.

The term "consisting of" describes aspects of the invention in which only those features explicitly recited in the claims are included and thus other components or process steps not explicitly or inherently included in the claim are excluded.

As used herein, the term "compound" is intended to refer to a chemical entity, whether in the solid, liquid or gaseous phase, and whether in a crude mixture or purified and isolated. The term "derivative" or "analog" refers to a chemically modified version of a chemical compound that is structurally similar to a parent compound, including polymeric forms, matrices and grafts.

The term "polymer" describes a stable combination of covalently bound repeating units termed "monomers". The monomers of identical structure form a homopolymer, while more than a single monomer form a "co-polymer".

The term "grafted polymer" describes a homopolymer or a co-polymer where a modifying group derivatizes all or some of the monomers.

The term "matrix" describes a three-dimensional structure made of a polymer, with available space to situate chemical moieties of the nature different from the polymer forming the matrix frame.

The term "cross-linker" describes an agent connecting individual polymer chains in a matrix formation.

The term "probe" describes a molecule interacting with a target analyte and producing a detectable and interpretable signal. The probe may have a particular chemical formula or structure and may exist in monomeric, oligomeric or polymeric form, and/or may be substituted or derivatized.

The term "chelator" describes a molecule that forms multiple donor-acceptor bonds with the bound central atoms by groups that are side chains or substituents of the same molecule, such that the resulting bond is especially strong and may have multiple character, e.g., a combination of covalent and dative bonds and/or a multiply covalent bonds. A chelator moiety may be a probe or may not be a part of analysis, without limitations.

The term "colorimetric" describes the probe signal comprising visible spectral shift, a change of color.

The term "naked eye" describes a detection of the signal organoleptically, e.g., without use of an optical instrument.

The term "alkyl", as used herein, unless otherwise specified, refers to a straight, branched, or cyclic hydrocarbon fragment. Non-limiting examples of such hydrocarbon fragments include those having 1 to 32 carbon atoms and specifically include methyl, ethyl, propyl, isopropyl, butyl, isobutyl, t-butyl, pentyl, isopentyl, neopentyl, hexyl and the like.

As used herein, the term "cycloalkyl" or "cyclic hydrocarbon" refers to a cyclized alkyl group.

The term "aryl", as used herein, and unless otherwise specified, refers to an aromatic group containing only carbon in the aromatic ring(s), such as phenyl, biphenyl, naphthyl, anthracenyl, and the like.

The term "heteroaryl" refers to an aryl group where at least one carbon atom is replaced with a heteroatom (e.g. nitrogen, oxygen, sulfur) and includes, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, and the like.

The term "arylalkyl" as used in this disclosure refers to a straight or branched chain alkyl moiety having 1 to 32 carbon atoms that is substituted by an aryl group or a substituted aryl group having 6 to 12 carbon atoms, and includes benzyl, 2-phenethyl, 2-methylbenzyl, 3-methylbenzyl, 4-methylbenzyl, 2,4-dimethylbenzyl, 2-(4-ethylphenyl) ethyl, 3-(3-propylphenyl)propyl.

As used herein, the term "substituted" refers to at least one hydrogen atom that is replaced with a non-hydrogen group, provided that normal valencies are maintained and that the substitution results in a stable compound.

The present disclosure is further intended to include all isotopes of atoms occurring in the present compounds. Isotopes include those atoms having the same atomic number but different mass numbers. By way of general example, and without limitation, isotopes of hydrogen include deuterium and tritium. Isotopes of carbon include $^{13}C$ and $^{14}C$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

3-HNHBH Probe, Derivatives and Conjugates

Practicing the embodiments of the method comprises procuring the probe in a form adequate to the specific embodiment, contacting an analyte with the probe, and measuring the emerging colorimetric signal. The probe (e.g., a compound of particular chemical formula described hereinafter) can be in a soluble monomeric form, dimeric form, oligomeric, aptameric, serve as a grafting moiety on a polymer, be a co-monomer, be entrapped in a gel or rigid network, and/or be non-covalently absorbed by a hydrophobic surface. Depending on physical and chemical forms, the probe and its derivatives are suitable for direct addition to a spectrophotometric cuvette, use in indicator strips, lateral flow devices, microfluidic devices, probe arrays, "Lab-on-paper" devices, stand-off methods, and in multiplex methods and in multistage tandem methods without limitation.

The synthetic route to 3-HNHBH is disclosed in P. Melnyk, V. Leroux, C. Sergheraert, C. and P. Grellier *Bioorganic & medicinal chemistry letters*, (2006) 16(1), pp. 31-35, incorporated herein by reference in entirety and referred to as "Melnick et al" below.

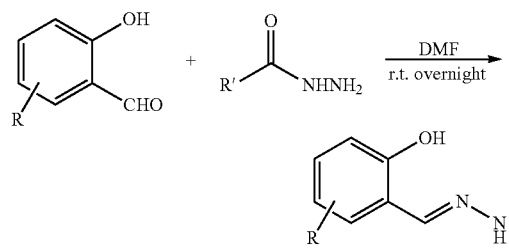

With R being H, vinyl, alkene, allyl, diene, dienophile, alkyne, a polymeric network, the synthetic route to 3-HNHBH or its polymers, grafts, derivatives and conjugates starts with 2-hydroxy-4-vinylbenzaldehyde (C=CC1=CC(=C(C=C1)C=O)O). Under the mild conditions of Melnick et al. 2-hydroxy-4-vinylbenzaldehyde can be reacted with 4-hydroxybenzohydrazide, leaving the moiety R intact and obtaining the product of Melnick et al.

To practice other embodiments as described above, the colorimetric probe can be included as a cross-linker or substituent in a polymer matrix. Non-limiting examples of such active cross-linkers are incorporated herein by reference as WO18162396 disclosing the process of obtaining a copolymer through polymerization of at least two types of monomers, one—a hydrazine colorimetric probe and another a para-phenylamine. The hydroxyl groups on the phenyl rings of 3-HNHBH are suitable for selective activation when the 3-hydroxy group adjacent to the hydrazine scaffold of 3-HNHBH is passive or protected. The group is important in Cu(II) chelation process and needs to be de-protected after incorporation of the colorimetric cross-linker in the matrix. The protection of the hydroxy-hydrazine moiety is achievable by complexation with multivalent ions, while phenol hydroxyls can be rapidly reacted with the silanized support producing the polymer matrices, dendrimers, gels, aptamers and other higher-order constructs without limitation.

Alternatively, the vulnerable hydroxy group of 3-hydroxyhydrazine, central for the function of the probe (below), can be protected by complexation with a transition metal as described in US20120164027 incorporated herein by reference in entirety. The probes can be assembled in a polymer network by a bis-acrylamide/acrylamide cross-linker utilizing radical polymerization. At a later stage, the emergent chromogenic matrix can be dissociated from the protecting cation by chelators and/or acids which in turn can be removed by washing. The batch of the matrix needs to be standardized and calibrated by Cu(II) aliquots. The process described herein is not limiting and other chemistries—for example, click chemistry and other protection schemes or absence thereof are conceivable within the scope of the present invention. The sequences of protection steps described in the paragraphs above might be difficult for implementation and alternative synthetic routes are possible.

A drawback of protection by chelation is steric entrapment of the ions in the domains with a high content of crosslinker that would arise stochastically during radical polymerization. Such trapping would produce batch-to-batch variations in the background and would require more complex standardization to practice the inventive method.

An alternative synthetic route begins with 4-vinylbenzene-1,2-diol (3,4-dihydroxystyrene, C=CC1=CC(=C(C=C1)O)O), available through MuseChem, Founder Pharma, Ambeed and other vendors. The phenol hydroxyls are protected by tetrafluoropyridyl (TFP) group. TFP can be installed in one step with no sensitivity to water or air, and it is stable under a range of commonly employed reaction conditions including acid and base:

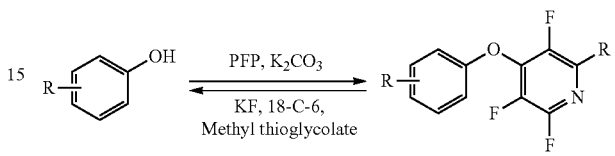

The TFP protecting group is readily cleaved under mild conditions with quantitative conversion to the parent phenol, observed in many cases in less than 1 hour (See W. D. Brittain and S. L. Cobb, *Organic & biomolecular chemistry*, 2019, 17(8), pp. 2110-2115, incorporated herein by reference in entirety). Alternatively, acetic anhydride in pyridine solvent can be used for protection followed by enzymatic deprotection (See L. Sánchez-Barrionuevo, A. González-Benjumea, A. Escobar-Niño, M. T. Garcia, O. Lopez, I. Maya, J. G. Fernandez-Bolanos, D. Canovas, and E. Mellado, *PloS one*, 2016, 11(11), p. e0166561, incorporated herein by reference in entirety). Protection of catechol hydroxy groups is necessary due to free-radical reactivity under the conditions of immobilization via vinyl moiety of the styrene ring in 3,4-dihydrostyrene. After attachment to the desired substrate or forming a desired conjugate, the deprotected and bound 3,4-dihydrostyrene is converted into polymer-bound form of 2-hydroxy-benzaldehyde (salicylaldehyde), which in turn is a precursor for 3-HN-TBH, according to the synthetic route of Melnick et al.

The immobilized 2-hydroxybenzyl alcohol (saligenin, salicyl alcohol, C1=CC=C(C(=C1)CO)O) is catalytically oxidized in air to give 2-hydroxybenzaldehyde. The oxidation of the hydroxybenzyl alcohols is also carried out in an aqueous solution with a platinum-lead-carbon catalyst and gives the corresponding hydroxybenzaldehydes in yields of more than 98% (See F. Bruhne, E. Wright, Benzaldehyde. *Ullmann's Encyclopedia of Industrial Chemistry* 7th ed. (1999-2017), NY: John Wiley & Sons. Online Posting Date: Oct. 15, 2011, incorporated herein by reference in entirety). The in-situ formed 2-hydroxybenzaldehyde is subsequently reacted with 4-hydroxybenzohydrazide according to the Melnick scheme above.

The resulting approach is a preferred embodiment since the presence of a vinyl moiety on the precursor combined with protection of vulnerable catecholic hydroxyls allows versatile covalent immobilization schemes—such as conjugation to polymer chains, nanoparticles, microbeads, membranes, gels, multi-well trays, dendrimers, aptamers without limitation. The volume concentration of a metal-binding moiety in such matrices can be high and due to the presence of intramolecular assistance effects, such concentrated ligand matrices allow for much higher affinities to the target ion than is possible with a detached monomer. The intramolecular assistance is observed when the distance between the adjacent 3-HNHBH groups is smaller than the length of a diffusional leap for Cu(II) at a given temperature. Typically, binding by an isolated monomeric chelator is accompanied by entropy cost due to a reduction in the number of microstates imposed by a constrain on rotational and vibrational degrees of freedom existing on the ligand side prior to chelation. Also, the presence of a solvation shell around the ion disrupts the regular hydrogen bond network structure in the solvent, increasing entropy. Loss of solvation shell would have decreased entropy. This entropic term on the ion side is also minimized during chelation, due to the loss of solvation shell. When multiple chelator groups are in proximity, the dissociated ion is instantly re-complexed by the neighbors. Because the new orbital overlap is virtually instant, the next binding neighbor group does not have time to experience an ensemble of microstates associated with entropy increase and the ion does not have time to re-gain its solvation shell. Thus, the binding thermodynamics in such dense ligand matrices changes dramatically, reducing the binding affinity thresholds by orders of magnitude as compared to a monomeric ligand form.

The conjugating moiety is not limited to vinyl or to radical polymerization chemistry of conjugation. Dienes, dienophiles, alkynes, isocyanates, epoxides, diazonium groups are highly reactive, and some can survive protection of reactive hydroxy groups in saligenol precursor as described above, especially alkynes and dienes capable of one-pot click chemistry. Such immobilized 3-HNHBH probes have multiple applications producing economical, sensitive and portable embodiments, superior to the competing methods.

In still further embodiments, unmodified 3-HNHBH can be entrapped in polymer matrices without the need for chemical derivatization. One method of entrapment depends on a hydrophobic adsorbent (hydrophobic silica) in intimate contact with a cellulose powder. Such a heterogenous blend allows effective immobilization of the hydrophobic ligand on silica and at the same time allows wicking of the analyte solution through the hydrophilic cellulose microdomains. The release matrix composition is not limiting and other embodiments are possible.

In a preferred embodiment, a hydrophobic-core carrier comprises a carrier, and a plurality of hydrophobic groups covalently linked to the polymeric carrier. The hydrophobic groups are capable of dissociably linking load molecules. A polymeric carrier comprises a backbone wherein the carrier is polylysine, polyaspartic acid, polyglutamic acid, polyserine, polythreonine, polycysteine, polyglycerol, polyethyleneimines, natural saccharides without limitation; wherein each hydrophobic group has a molecular weight of less than 1,000 Daltons independent of the carrier molecular weight, wherein the hydrophobic group is linear alkyl, branched alkyl, phenyl, naphthyl, cholesterol, vitamin D, and/or vitamin E (See US2017/0368190A1 incorporated herein by reference in entirety). The number and molecular weight of the pendants in the matrix of the US '190 publication would determine the rate of release that can be made negligible despite the absence of covalent attachment. The presence of hydrophilic components allows capillarity and wicking of the ion-carrying solution through the mixed polar-nonpolar matrix in a context of a lateral flow device, while the presence of hydrophobic components allows for probe immobilization. Caution needs to be exercised to ensure the absence of non-specific Cu(II) binding to the functionalizing groups in the bibulous layer of the lateral flow devices. Dies, conjugates systems, derivatized porphyrins may be utilized for producing strongly hydrophobic micropatterns. However such putative 3-HNHBH traps may interact with the probe electronically, altering its spectra too unpredictably and can sequester Cu(II) ion in direct competition with the probe. Generally, the change in environment's polarity would cause Stock's shifts in the shape and peaks of the spectra, that need to be accounted for by calibration.

Yet non-limiting additional examples of acceptable non-covalent binding systems are available for reversible immobilization of low molecular weight assay reagents in multi-zone test devices. The suitable non-polar modifiers are hydrophobin proteins (US2005/238685), a layer that includes: agarose and/or at least one derivative, and at least one polyethylene glycol and/or at least one derivative (WO09098123A1), an amphiphile reversibly bound to a substrate by non-covalent interaction, preferably by polar interaction, the amphiphile is a bolaamphiphile, such as pentamidine (U.S. Pat. No. 6,444,321), carboxylated polyvinylidene fluoride support (U.S. Pat. No. 6,037,124), matrices including crosslinked agarose, crosslinked dextran, crosslinked cellulose, crosslinked dextran and bisacrylamide, or matrices based on silica or plastic polymers (U.S. Pat. No. 6,150,151), starch derivative with a functional group for non-covalent binding (US2006/183697), the composite surface modifiers (US2018/298154), all above incorporated herein by reference in entirety.

The covalently and non-covalently entrapped 3-HNHBH finds utility in reflectometric stand-off, lateral flow, array, microfluidic, flow cytometry, "lab-on-paper" and tandem column analytical sensors.

Preprocessing of the Sample

The method of invention is carried out by first identifying the analyte-carrying sample, making decisions on the desired fractional analysis or the analysis of the total content, optionally pre-processing the sample to release the analyte, optionally separating the debris, optionally eliminating turbidity, mechanical impurities, precipitates, potential oxidants and reducers that may interfere with the probe and the ion and bringing the pH as well as solvent composition to a target range. Pre-processing may include affinity and ion-exchange trapping and pre-concentration of the target ion. Depending on the purpose of the analysis and the composition of the analyte, different embodiments of the method become most suitable for the specific contexts. Decision-support tools are helpful at this stage (see below). The analyte samples can originate in living tissues, cell and bacterial culture, food products, drinks and supplements, industrial, artesian, fracturing and recycle water, as well as water-organic mixes and each composition requires an optimal path to the result.

Preprocessing may include separation of the debris from the mostly aqueous media, rinsing and extraction of the debris by an aqueous buffer and merging the fractions. In some embodiments, only the removal of the dispersed matter happens. In other embodiments, osmotic shock, sonication, thermal treatment may be used for the complete release of Cu(II). In further embodiments, intense solvent processing including extraction and re-extraction is required to isolate the polar fraction with the content of the analyte Cu(II) proportional to the initial content in the entirety of the system. In still further embodiments, the release of Cu(II) from other chelators or oxidation of Cu(I) into Cu(II) can occurs. In yet other embodiments use of surfactants, chelators, chaotropic agents, milling, microwave processing, boiling with nitric and chloric acids, sample incineration and ash dissolution followed by reversible ion-exchange separation also occur. Such sample preparation can be conducted by the methods well-known to the skilled in the art, for example as described (See S. Mitra, editor. *Sample preparation techniques in analytical chemistry*. John Wiley & Sons; 2004; J. Pawliszyn, editor. *Sampling and Sample Preparation in Field and Laboratory: Fundamentals and New Directions in*

Sample Preparation. Elsevier; 2002; Z. Mester, R. E. Sturgeon, *Sample preparation for trace element analysis*. Elsevier; 2003; J. R. Dean, *Methods for environmental trace analysis*. John Wiley and Sons; 2003, all incorporated herein by reference in entirety).

Such pre-processing may involve subjecting of the sample to any method known to the skilled in the art without limitation such as membrane filtration, centrifugation, evaporation, solvent extraction, freezing out. A preferred non-limiting pre-processing method is a standardized one, such as pressing of the aqueous analyte through a polymer and inert ultrafiltration membrane such as Teflon or PVDF. Exemplary membranes are ZeeWeed 1500 Ultrafiltration (UF) Membrane; Ultrafiltration SFP-2880 by DuPont; Microdyn Nadir Membrane Filters, UV150; Steridyne—Meissner Filtration Products; Pegasus™ Prime Virus Filter and many more without limitation. Ultra-pores are in the optimal pore range, since reverse osmosis would distort the concentration of copper (II) ions and micro-pores may not suffice for the elimination of the Tindall's optical effects produced by colloids.

Purified sample can further be pre-tested to ensure that oxidation state is not deleterious for the probe, which can be oxidizable by reactivity of hydroxy-hydrazones with nitrites, sulfonamides, hypochlorites, peroxides, multivalent transition metals such as Cr, Ce, Mn, elementary halogens, ozone, Ag+. The oxidized probe will be unsuitable for the complexometric detection of Cu(II). Alternatively, a strongly electron-donating environment is capable of reducing oxy-hydrazine moiety as well as Cu(II) itself and the redox potential needs to be monitored from the reducing side as well.

A iodide-starch paper indicator, a redox electrode pair or colorimetric pH-independent and pH-dependent tests can produce the desired red-ox measurement without limitation. Non-limiting examples of the preferred pH-independent colorimetric agents are: 2,2'-bipyridine (Ru complex) +1.33 eV, colorless to yellow, N-phenylanthranilic acid +1.08 eV, violet-red to colorless, o-dianisidine +0.85 eV, red to colorless, Sodium diphenylamine sulfonate +0.84 eV red-violet to colorless, diphenylbenzidine +0.76 eV violet to colorless, diphenylamine +0.76 eV violet to colorless, Viologen −0.43 eV colorless to blue. A small aliquot of the sample can be separated from the bulk of the sample, added to the red-ox indicator which was stored properly according to the instructions and the color change of interest or absence of color change would indicate the presence or absence of oxidants and reductants incompatible with the stability of the inventive probe or the target ion.

The binding constant of the ligand to the ion of interest depends on pH and selectivity toward interfering species and therefore depends on protonation of the 3-hydroxy group adjacent to the hydrazine scaffold of the probe. The acidity of the sample is measured by separating a pre-defined aliquot and assessing pH electrochemically by an electrode pair, by colorimetry using pH indicator paper or by mixing with a soluble pH indicator. The preferred embodiment without limitation is Universal Indicator by Yamada, typically containing or consisting of water, propan-1-ol, phenolphthalein sodium salt, sodium hydroxide, methyl red, bromothymol blue monosodium salt, and thymol blue monosodium and changing color in distinct easily observable ranges of pH (for the recipes for Yamada's and other universal indicators, see L. S. Foster and I. J. Gruntfest, *Journal of Chemical Education*, 1937, 14 (6): 274. incorporated herein for reference in entirety).

Colorimetric analysis by the inventive method is may be initiated and proceed correctly if the controlled parameters above are in the range, see more details below.

Conducting Measurements

Depending on the specific analyte samples, different embodiments are preferred for practicing the invention. In one embodiment, the pre-processed analyte is mixed with the probe in a cuvette of a spectrophotometer, the final pH and solvent composition are adjusted, residual turbidity is tested and ruled out or compensated. The Cu(II)-ligand spectrum is scanned to ensure it matches the absorption in its optimally tautomerized form recognizable by the spectrum shape as a function of scanning wavelengths. Intensity of Cu(II)-ligand absorption or residual transmittance are reported by the device and based on characteristics of the cuvette the analyte concentration is established by Lambert Law. A control cuvette is typically provided with the same sample components except for the probe. The necessary adjustments need to be introduced based on calibration data, produced by spiking the sample material with known aliquots of Cu(II) to allow internal control (See B. Dupré, J. Viers, J. L. Dandurand, M. Polve, P. Bénézeth, P. Vervier and J. J. Braun, J. J., *Chemical Geology*, 1999, 160(1-2), pp. 63-80. incorporated herein by reference in entirety). The necessary equipment required for practicing this embodiment is exemplified in M. M. Khalil, A. Shahat, A. Radwan and M. F. El-Shahat, M. *Sensors and Actuators B: Chemical*, 2016, 233, pp. 272-280; N. Kaur, S. Kumar, *Dalton Transactions*, 2006, (31):3766-71; S. Nohut, S. Karabocek, S. Güner and Y. Gök, *Journal of pharmaceutical and biomedical analysis*, 2011, 20(1-2), pp. 309-314; incorporated herein by reference in entirety. Use of spectrophotometric detection is more applicable to precise measurements of Cu(II) content in biological fluids, taken for diagnostic purposes, for cell culture media content, for precise microelement monitoring in the environment, for measurements of composition in foods, drinks, supplements and pharmaceuticals.

Yet in other embodiments, the measuring device is a reflectometer, measuring not transmitted but reflected and scattered components of the spectrum. In the embodiments of reflectometry no cuvettes are required. One benefit of using reflectometry is the possibility to procure and analyze the data remotely, simultaneously and from multiple sources (See C. L. Morais, L. C. D. Silva, N. A. Pinheiro, F. G. Menezes and K. M. Lima, *Journal of the Brazilian Chemical Society*, 2017, 28(12), pp. 2506-2513; herein incorporated by reference in entirety). The advantage of reflectometric detection is the ability to conduct stand-off measurements under the conditions of a suspected toxic atmospheres, the proximity of fire, explosives, combustibles, or extensively over broad areas. Reflectometric measurements can be conducted from cutters, helicopters, drones. Immobilized probes on small pieces of floating material can be scattered over the suspected area and monitored remotely and robotically, comparing the color changes with the library of past controls stored in the memory units of the monitoring equipment.

In an alternative embodiment, the measurement is conducted by a standardized kit with instructions providing a flow-chart of situations applicable to sample pre-processing, aliquots of reagents stored in protective containers, miniaturized ultrafiltration unit, containers for mixing the reactants, paper indicator strips for pH and redox potential, paper indicator strips for Cu(II) and color palettes for interpretation of the signals. The paper strip of the kit is a dense cellulosic material capable of non-covalently absorbing the inventive probe.

To prepare such a strip, the probe is dissolved in THF to saturation, and both the solution and paper substrates are transferred in a noble gas atmosphere, where the solution is sparged by argon or nitrogen to remove the trace oxygen. The paper is soaked with the probe solution and the solvent is evaporated by the inert gas stream. The dried strips are individually coated in a thin transparent and oxygen-impermeable plastic, and bundles of 5-10 pieces are also placed in sealed metal foiled envelopes filled with a desiccator material. With such a design of tare, the probe is protected from the diffusion of oxygen, water vapor and UV light and can be stored for an extended time in a ready for use form. In operation, the foil envelopes are unsealed, the individual strip that is used immediately is incised on the edge, exposing uncoated cross-section to submerge in the analyte. The purified and pH-adjusted aqueous phase is contacted by a paper strip and the extent of color development is observed by a naked eye. The analyte solution may be carried by capillary wetting along the porous flat conduit or pad in the length dimension of the strip.

In an alternative embodiment, the analyte accumulates in the perpendicular section (band) of the strip provided with immobilized probes (lateral flow devices). Concentrating all analyte existing in the tested pre-defined volume in one narrow band on the strip produces a strong colorimetric signal. Such an analyte-concentrating section of the device is produced by enclosing in the lateral flow path a matrix that is permeable to the solvent and can either covalently or non-covalently entrap 3-HNHBH (see above) or, more generally, the compound of formula (I).

The intensity developed in the band is compared with a provided color palette and a wide possible range is reported. Alternatively, the band is scanned by a video-camera and the result is computationally processed. Alternatively, the processing is conducted remotely and/or assisted by a computational network. The necessary preliminary pH measurements are also conducted by Universal Indicator paper strips as a kit component. The kit embodiment is preferred for geological surveys, preliminary sample collection for more detailed in-house analysis, especially in challenging conditions or when equipment-occupied space or weight is constrained. Typically, a standardized and miniaturized analytical kit is more economical than a full-sized set of equipment.

WO08075193A2 discloses a lateral flow assay device producing a color when a metal ion reacts with a color-forming regent and the details of the analysis are incorporated herein by reference in entirety. The technology is applicable to Cu+2. Other non-limiting examples of devices utilizing immobilized probes include R. Sheng, P. Wang, Y. Gao, Y. Wu, W. Liu, J. Ma, H. Li and S. Wu, *Organic letters,* 2008, 10(21), pp. 5015-5018; Y. Takahashi, H. Kasai, H. Nakanishi, and T. M. Suzuki, T. M., *Angewandte Chemie International Edition,* 2006, 45(6), pp. 913-916; Q. Lin, P. Chen, J. Liu, Y. P. Fu, Y. M., Zhang, T. B. Wei. *Dyes and Pigments,* 2013, 98(1):100-5; Y. Qian, L. Cao, C. Jia, P. O. Boamah, Q. Yang, C. Liu, Y. Huang and Q. Zhang, Q. *RSC Advances,* 2015, 5(95), pp. 77965-77972; N. Mergu and V. K. Gupta, V. K., *Sensors and Actuators B: Chemical,* 2015, 210, pp. 408-417; J. J. Xiong, P. C. Huang, C. Y. Zhang, F. Y. Wu., *Sensors and Actuators B: Chemical.* 2016. 226:30-6.

The immobilized (preferentially—covalently) 3-hydroxy-5-nitrobenzaldehyde-4-hydroxybenzoylhydrazone (3-HNHBH) probe can be used in colorimetric arrays intended for simultaneous detection of multiple ion species in the presence of each other, the color changes can be detected automatically by fiber optics (See R. P. Kingsborough, S. Giardini, D. J. Lee, J. H. Kim, K. Quigley, A. Stolyarov, L. Cantley, S. Tysk, C. Hennessy, M. Rothschild and R. Odessey, *Chemical, Biological, Radiological, Nuclear, and Explosives (CBRNE) Sensing XIX,* 2018, Vol. 10629, p. 106291E); M. Ariza-Avidad, A. Salinas-Castillo, M. P. Cuellar, M. Agudo-Acemel, M. C. Pegalajar and L. F, Capitan-Vallvey, *Analytical chemistry,* 2014, 86(17), pp. 8634-8641, incorporated herein by reference in entirety).

The detection step for each array position may be provided with computer-assisted interpretation of the colorimetric information and such information will be processed by an integrating algorithm, since at the given exposure (pH, temperature, solvent) some of the complexations simultaneously present on the array would generate distorted optical signals vs. individual detections under completely optimal conditions. The algorithm accounts for these discrepancies based on the programmed library of detection events and based on optimal responses to variable ratios of the ion species, detection pH and solvent compositions. The enabling details of such computer-assisted vision methods are incorporated herein by reference in entirety (See L. F. Capitan-Vallvey, N. Lopez-Ruiz, A. Martinez-Olmos, M. M. Erenas and A. J. Palma, *Analytica Chimica Acta,* 2015, 899, pp. 23-56; D. J. Soldat, P. Barak and B. J. Lepore, *Journal of chemical education,* 2015, 86(5), p. 617).

Another embodiment of array-based Cu(II) detection is the immobilization of Cu-selective probes on microbead arrays and subjecting the library to flow cytometry. The benefits of using flow cytometers are economical, these devices are multi-functional and in the absence of Cu(II) analysis can be immediately used for blood, cell-culture, emulsion and other analyses without limitation. The probes for Cu(II) selective determination can be synthesized on the beads in-situ, can be entrapped in the beads or can be grafted on the beads in the final molecular form. Alternatively, the Cu(II) probes can saturate different aliquots of the living cells intended for colorimetric detection of Cu(II), penetrating through the membranes and cell walls (See N. M. Franklin, J. L. Stauber, R. P. Lim, *Environmental Toxicology and Chemistry: An International Journal.* 2001, 20(1). 160-70; incorporated herein by reference in entirety). Other probes suitable for colorimetric Cu(II) detection include azobenzenes, rhodamines, pyrenyl-azadienes, Ru(I)-phthalocyanine and may more without limitation. (See T. Gunnlaugsson, J. P. Leonard, N. S. Murray. *Organic letters.* 2004, 6(10):1557-60; V. K. Gupta, N. Mergu, L. K. Kumawat, *Sensors and Actuators B: Chemical.* 2016, 223, 101-13; R. Martinez, A. Espinosa, A. Tarraga. and P. Molina, *Tetrahedron,* 2010, 66(21), pp. 3662-3667; M. S. Rodríguez-Morgade, M. Planells, T. Torres, P. Ballester, E. Palomares, *Journal of Materials Chemistry,* 2008, 18(2), 176-81, incorporated herein by reference without limitation). In still another embodiment, two or more probes can be allowed to diffuse across the membranes of target cells to ensure the maximal ratio of true to false positives, especially at the lower boundary of Cu(II) detection range. Additionally, the multiplex signal originating from multiple probes differentially sensitive to a plurality of interferents is more objective than the signal from a single probe system. In still other embodiments, the bead arrays can be prepared for simultaneous detection of multiple ions by flow cytometry, including competing species for Cu(II). In a preferred embodiment, the entire massive of data can be processed simultaneously, with each colorimetric value for each ion assisting in the interpretation of remaining values representing the sums of the target signals and the interfering signals.

Yet another embodiment entails single and multiplex confocal microscopy use of colorimetric Cu(II) probes. The cell culture of interest is grown in Petri dishes or in 96-well plates and the serum-containing media is replaced by a serum-free media with the probes of interest including 3-HNHBH, that would diffuse across the cell membranes and accumulate in the organelles enriched in Cu(II). The identity of the signals is validated by simultaneous or parallel use of 2-3 probes concentrating in the same regions. The non-limiting examples of the method are illustrated by U.S. Pat. No. 7,659,991; H. H. Wang, L. Xue, Z. J. Fang, G. P. Li and H. Jiang, *New Journal of Chemistry*, 2010, 34(7), pp. 1239-1242; D. Maity, A. Manna, D. Karthigeyan, T. K. Kundu, S. K. Pati and T. Govindaraju, T. *Chemistry—A European Journal*, 2011, 17(40), pp. 11152-11161, all incorporated herein by references in entirety.

Still another embodiment of colorimetric approach is "Lab-on-paper" devices that combine colorimetric and electrochemical layers, with the microchannels and micro-chambers performed in a special dense chemical fiber-based material, with all illustrative examples incorporated herein by reference in entirety. Non-limiting illustrations of this technology are provided in US20160339428 disclosing a method for forming a chemically patterned paper microfluidic device (cPMD) having controllable hydrophobic regions enabling point of care sensor devices. The disclosed invention comprises multilayer strip, providing for various molecules to be immobilized with charge interaction. The paper-based microfluidic platform as disclosed is repeatable, versatile, cost-effective, and allows for the creation of complex channels using the settling time calculated from calibration results. The disclosed system supports a wide variety of scenarios for testing, diagnostics and drug delivery, and related products and services. The inventive ligand can be incorporated in the colorimetric zones of the device in '428. The copper results are presented in FIG. 3 of the incorporated disclosure. The copper ion detection results showed a linear trend where colorimetric integration density increases with ion concentration.

P. Rattanarat, W. Dungchai, D. Cate, J. Volckens, O. Chailapakul and C. S. Henry, *Analytical chemistry*, 2014, 86(7), pp. 3555-3562. illustrates combined colorimetric and electrochemical microfluidic paper-based analytical devices (mPAD) in a three-dimensional configuration, also incorporated herein by reference. The device separates colorimetric detection on one layer from electrochemical detection on a different layer. Separate detection layers allow different chemistries to be applied to a single sample on the same device. To demonstrate the effectiveness of this approach, colorimetric detection is shown for Ni, Fe, Cu, and Cr and electrochemical detection for Pb and Cd. Detection limits as low as 0.12 µg (Cr) were achieved on the colorimetric layer while detection limits as low as 0.25 ng (Cd and Pb) were achieved on the electrochemical layer. Selectivity for the target analytes was demonstrated for common interferences. The 3-HNHBH (e.g., or compound of formula (I)) probe can be incorporated in the colorimetric section of the microfluidic device and the reported detection limit (below) for Cu(II) and 3-HNHBH approximately matches the ones for this technology and can further decrease in dense 3-HNHBH matrices, as analyzed above. Combining the outputs of the different nature in an integrated signal makes detection more robust and precise while being economically efficient. Additional economic benefit is produced by the applicability of the same measuring sensor kit to multiple ions typically co-occurring in industrial waters, aquifers, fracking fluids, geological deposits, oceanic and sea regions slated for pollution monitoring etc.

Still another embodiment entails tandem methods when the copper (II) ion is concentrated by the first method (preferably ion-exchange and/or affinity chromatography and/or capillary electrophoresis) and is re-directed to the second stage comprising a detection method. The tandem methods are advantageous at the trace levels of analytes when the concentration capability of a single method is reaching a threshold. Without limitation, the inventive tandem methods include capillary electrophoresis—cPMD pair, ion exchange chromatography—colorimetric fiber-optic array pair, affinity chromatography—lateral flow device pair. The enrichment factor for dilute analytes can reach many orders of magnitude, for example, a volume of a dilute Cu(II) present in an aquifer might be 1 liter, 10 liters or more per an affinity column. The volume of the sample is limited by the capacity of the column, availability of the free binding sites and concentration of the bound ion, equilibrating with the load. The volume of the eluent can be 1 ml, 0.1 ml or lower without limitation. The ratio of the feed volume to the eluent volume is proportional to the enrichment factor at the first stage and reaches $10^5$-$10^6$ as per the non-limiting examples above. The volume absorbed by a lateral flow device can be 1-2 ml, the volume of the chromogenic matrix producing the signal can be 0.01-0.02 ml or less. The ratio of the absorbed volume to that of the chromogenic matrix produces the enrichment factor at the second step. A broad range of enrichment factors for the two-step separation reaches $>10^5$, preferably $>10^6$, even more preferably $>10^7$, $>10^8$, $>10^{10}$. With such a range of enrichment factors, simple tandem procedures as described herein become very economical as compared to the competing fluorimetry and mass-spectroscopic approaches. While the latter exceeds the inventive method in sensitivity and operates in one step, the capital costs, exploitation costs, bulk and complexity of the equipment form the downside, which is likely to outweigh the benefits of the competing methods in most of the situations.

Another benefit of tandem methods is the separation of chromogenic oxidant species. While pre-testing procedure was considered earlier in the Preprocessing section, the former cannot prevent the residual presence of oxidants or the presence of unexpected oxidant species with the transition potential outside of the redox indicator range. Many oxidant species produce colored complexes and reaction products with the substituted hydrazide scaffolds and such probes can be used as one-time sensors for the oxidizers (see WO18162396 incorporated herein by reference). For the purposes of the present invention, non-limiting examples of oxidizing anions include nitrite ($NO_2$), periodate ($IO_4$), permanganate ($MnO_4$), hypochlorite (ClO) and peroxides. In a preferred embodiment, said change in color occurs when nitrites ($NO_2$) are present in the medium. Such oxidizing species may develop at the pre-processing step when the sample material is often extracted by detergents, chaotropic agents and subsequently is boiled in nitric acid to release transition metals that otherwise are sequestered in diverse non-specific binding sites. Such pre-processing routes are typical for the samples with the initial high solid content: living matter, sewage, geological samples and the ions of interest need to be separated first from the oxidized and hydrolyzed debris.

The affinity step allows the divalent cations to be selectively absorbed, while the oxidant anions will pass the column and the residual traces will be rinsed off by the washing step preceding the elution step. This capability qualitatively expands the range of environments amenable to the analysis by the present invention.

Even more preferred embodiment entails the use of pH variations and acid/base non-complexing buffers as eluents for the affinity-bound ions since this method does not introduce a potent chelating eluent that would have interfered with the analysis at the next stage. Non-limiting examples are acetate, propionate or formic acid buffers. The post-elution pH can be adjusted back to the optimal value for the development of the colorimetric signal. The two methods of the tandem interact productively in practical settings since the first step decreases the ratio of the interferents to Cu(II) and this ratio continues to decrease during the second separation step. Both steps taken individually will be incapable of providing the target decrease of interferents vs Cu(II) ratio necessary for detections when Cu(II) is a trace component and other species dominate.

In still another embodiment, the method of analysis is computerized. The analytical software can be uploaded on the local device such as a laptop, desktop computer or smartphone. Alternatively, the analytical software functions remotely. In still another embodiment, it is interactive with a supporting computational and reference network. Such decision-support communication is available via the Internet, Bluetooth, radio, satellite or fiber-optic links and includes a central processor with memory, preferably incorporated in a parallel computing grid. The purpose of communication is a remote analysis of the data, benefiting from the cumulative experience of multiple users. To practice the embodiment, locally measured parameters and digitized scans of the colorimetric spectra are transmitted to the processor. The centralized analytical system allows accounting for the deviations from the ideal conditions and deconvoluting the desired signal from the noise. The centralized remote analytical system compares the given transmitted pattern with the numerous analogous patterns for the same class of devices and eliminates false positives and false negatives more accurately than a local human operator. The algorithm of the central processor allows the a-priori analysis of suitability of the inventive analytical method to the specific conditions, assuming the suspected competing ions, the concentration of such ions, solvent composition, the presence of chelators and oxidant interferents, pH and temperature. In operation, the central processor sends the systematic list of queries to the user and only after receiving the replies indicating the completion of the preliminary and the measurement steps, it provides an accurate interpretation of the Cu (II) measurement. (See A. Malanoski, B. Johnson, J. Erickson and D. Stenger, *Sensors*, 2016, 16(11), p. 1927; A. K. Yetisen, J. L. Martinez-Hurtado A, Garcia-Melendrez, F. da Cruz Vasconcellos and C. R. Lowe. *Sensors and Actuators B: Chemical*. 2014, 196, 156-60; Y. Wang, Y. Li, X. Bao, J. Han, J. Xia, X. Tian, L. A. Ni, *Talanta*. 2016, 160, 194-204, all incorporated herein by reference in entirety).

EXAMPLES

Below provided the Examples illustrating the principles and experimental data supporting the analysis, the examples are provided herein for purposes of illustration only and are not intended to be limiting unless otherwise specified.

Example 1: Forming of 3-HNHBH-Cu(II) Complex

All solvents and reagents used were of HPLC grade and used without further purifications. Metal precursors used included nickel(ii) acetate, copper(ii) acetate, magnesium acetate, calcium acetate, palladium(ii) acetate and zinc(ii) acetate. Synthesis of 3-hydroxy-5-nitrobenzaldehyde-4-hydroxybenzoylhydrazone (3-HNHBH) ligand was conducted following an already reported procedure and then tested with precursors of nickel(ii), copper(ii), magnesium(ii), calcium (ii), palladium(ii) and zinc(ii) ions. (See P. Melnyk, V. Leroux, C. Sergheraert and P. Grellier, *Bioorg. Med. Chem. Lett.*, 2006, 16, 31-35; and A. A. Tameem, A. Salhin, B. Saad, I. A. Rahman, M. I. Saleh, S.-L. Ng and H.-K. Fun, *Acta Crystallogr., Sect. E: Struct. Rep. Online*, 2007, 63, o57-o58, each incorporated herein by reference in their entirety). Spectroscopic $^1$H NMR and EDX were used to check the chemical conformation and purity of the ligand before and after complexation with the metal ions, whereas UV-Vis spectroscopy was used to investigate the nature of complexation between the metal ions and the ligand. The UV-visible spectra were recorded on a Shimadzu UV-1601PC spectrophotometer with quartz cells of a 1 cm path length. The $^1$H nuclear magnetic resonance (NMR) spectra were obtained on a Bruker AV-500 spectrometer in dimethyl sulfoxide (DMSO-$d_6$) using tetramethylsilane (TMS) as an internal standard. All measurements were performed at room temperature. Scanning electron microscope (SEM) equipped with energy-dispersive X-ray spectroscope, EDX (Genesis-2120 Emcrafts, Korea Republic) was used to check the purity of the ligand and the ligand-metal complexes.

The solutions of 3-HNHBH ligand with tetrahydrofuran ($2\times10^{-4}$ M) and acetonitrile ($2\times10^{-3}$ M) were prepared and kept under sonication for 10 min. Thereafter, 10 mL of each metal precursor solution was added to 1 mL of a 3-HNHBH ligand solution in a clean glass vial. The resulting mixture was shaken, and changes in color were observed. Another 10 mL quantity of the metal precursor solution was added, and the process carried out again. A similar experiment was conducted with the metal precursors dissolved in THF. For the spectroscopic characterization, 2.5 mL THF was added to 0.5 mL solution of 3-HNHBH ligand in THF ($2\times10^{-4}$ M) in a quartz cell, and UV measurements were carried out. Metal precursor solutions in THF were added to the ligand solution in 10 mL aliquots in a quartz cell and the spectra were taken after each addition. For $^1$H NMR measurements, ligand and metal precursor solutions were prepared in DMSO-$d_6$ ($2\times10^{-3}$ M) in a 1:1 ratio. The ligand-metal complex was made by mixing equivolume solutions of the ligand and metal precursors, while the ligand was being analyzed directly.

Example 2: Selectivity Between Cu(II) Ion and Potential Interfering Species Competing for the Same Probe Full geometry optimization and vibrational frequency calculations of the free 3-HNHBH ligand and its metal complexes were carried out using the hybrid B3LYP density functional theory (DFT) approach and the 6-311+G(d) basis set. See A. D. Becke, *J. Chem. Phys.*, 1993, 98, 5648-5652; and C. Lee, W. Yang and R. G. Parr, *Phys. Rev. B: Condens. Matter Mater. Phys.*, 1988, 37, 785-789, each incorporated herein by reference in their entirety. Geometry optimizations of the ligand and complexes formed were carried out to the minima without imposing any constrains on the potential energy surfaces. Relative stabilities of the various forms of the ligand and the total energies of the natural bonding orbitals were obtained. The evaluated binding energies of the ligand and metal ions were obtained following the equation:

$$\text{Binding energy (BE)} = E_{comp} - (E_M^{2+} + 2 \times E_{lig}) \quad (1)$$

where $E_{comp}$ is the complex's total energy, $E_M^{2+}$ and $E_{lig}$ are the energies of the free metal ion and the free ligand, respectively. All calculations were conducted on GAUSSIAN 09 package. See M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, J. E. Peralta, F. Ogliaro, M. Bearpark, J. J. Heyd, E. Brothers, K. N. Kudin, V. N. Staroverov, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski and D. J. Fox, *Gaussian 09, revision b.* 01, 2009, incorporated herein by reference in its entirety.

Figure 1:
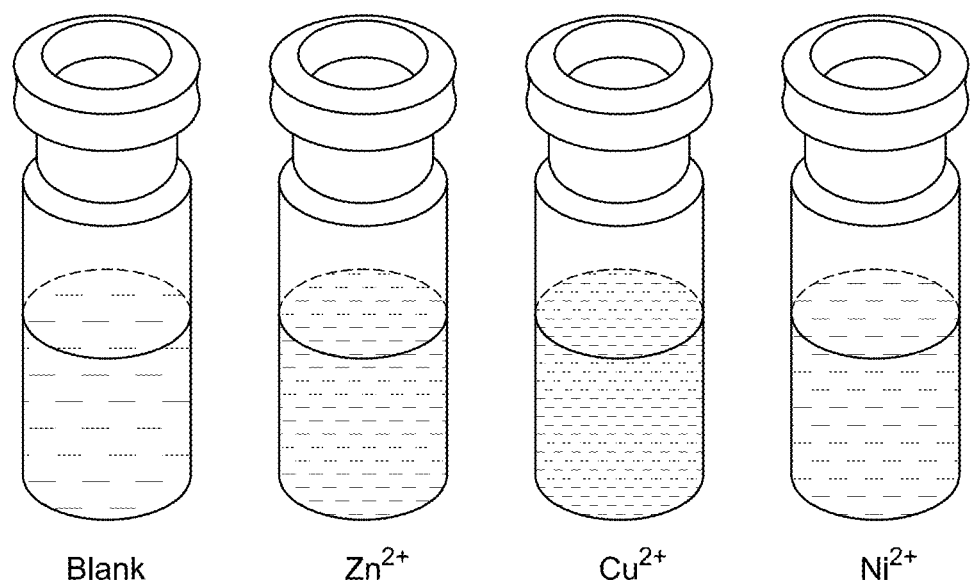
FIG. 1 illustrates color changes observed on addition of 3-HNHBH ligand to $Zn(OAc)_2$, $Cu(OAc)_2$ and $Ni(acac)_2$ solutions. The most intense color change was observed in the case of copper(ii) solution.
Figure 2A:
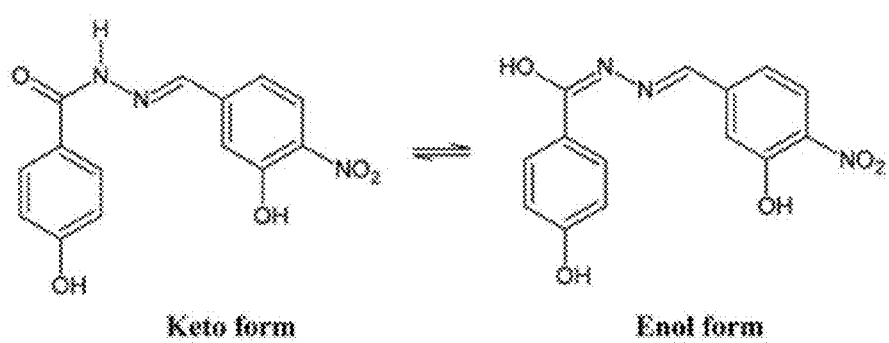
FIGS. 2A-2B illustrate (a) Keto-enol tautomerization of 3-HNHBH ligand, and (b) the proposed complexation mode of 3-HNHBH ligand with the metal ion center.
Figure 2B:
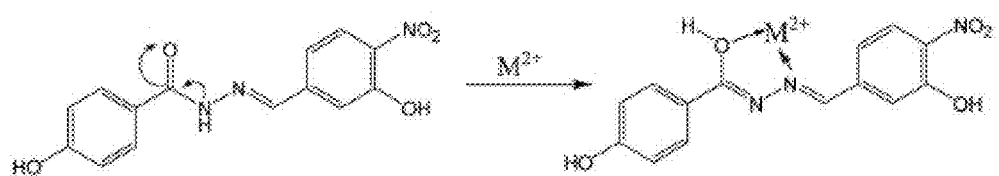

The selectivity of 3-HNHBH ligand towards a set of various metal ions including Mg(ii), Ca(ii), Ni(ii), Cu(ii), Zn(ii) and Pd(ii) was investigated. See Awual (2014); M. R. Awual, M. A. Khaleque, Y. Ratna and H. Znad, *J. Ind. Eng. Chem.*, 2015, 21, 405-413; M. R. Awual, T. Yaita, H. Shiwaku and S. Suzuki, *Chem. Eng. J.*, 2015, 276, 1-10; M. R. Awual, M. Khraisheh, N. H. Alharthi, M. Luqman, A. Islam, M. Rezaul Karim, M. M. Rahman and M. A. Khaleque, *Chem. Eng. J.*, 2018, 343, 118-127; M. R. Awual, M. M. Hasan, G. E. Eldesoky, M. A. Khaleque, M. M. Rahman and M. Naushad, *Chem. Eng. J.*, 2016, 290, 243-251; M. R. Awual and M. M. Hasan, *Sens. Actuators, B*, 2014, 202, 395-403; and M. R. Awual, M. M. Hasan and M. A. Khaleque, *Sens. Actuators, B*, 2015, 209, 194-202, each incorporated herein by reference in their entirety. It was observed that only the copper ion solution produced an intensive color change, while the rest of metal ion solutions showed a very mild alteration (FIG. 1) or almost no change in color. Hence, the combination of the ligand with copper ions was further investigated by spectroscopic and theoretical means. The 3-HNHBH ligand, like its 2-HNHBH analog reported in a previous study, exhibits two tautomeric keto and enol forms (FIG. 2A). See I. Abdulazeez, C. Basheer, A. A. Al-Saadi, *Journal of Molecular Liquids*, 2018, 264, 58-65, incorporated herein by reference in entirety. Hydrazonic ligands have been reported to exist as the keto form in the free state, while bind to metal ions in the enol tautomeric form (FIG. 2B). See M. V. Angelusiu, S.-F. Barbuceanu, C. Draghici and G. L. Almajan, *Eur. J. Med. Chem.*, 2010, 45, 2055-2062; and R. Gup and B. Kirkan, *Spectrochim. Acta, Part A*, 2005, 62, 1188-1195, each incorporated herein by reference in their entirety. From the $^1$H NMR spectrum of the pure ligand shown in FIGS. 3A and 3B, three distinct resonance peaks are observed at 11.86, 11.17 and 10.18 ppm chemical shifts which can be attributed to the phenolic and amide protons, respectively, indicating that the ligand is keto-tautomeric in a non-coordinated state. Upon complexation with the copper ion, however, a highly deshielded resonance peak at 12.64 ppm which is due to the enolic proton can be observed. This peak appears deshielded since the proton-bearing oxygen atom serves as one of the donor atoms during complexation with the metal ion as shown in FIG. 2B. The presence of the peak associated with the enolic proton confirms the tautomerization of the ligand to the enol form upon complexation. The UV-Vis absorption spectra of the ligand in THF showed an absorbance maximum at 347 nm ($\varepsilon_{347}$=4390 cm$^{-1}$ M$^{-1}$) due to a symmetry-allowed π→π* transition rather than a symmetry-forbidden n→π* transition. The presence of a single peak suggests the presence of an extended conjugation chain rather than two smaller resonance systems. In addition, two isosbestic points were observed at 315 and 383 nm in the colorimetric titration of the ligand with Cu(OAc)$_2$ (FIG. 4) indicating that there are only two absorbing species in the mixture (the free ligand and the ligand-metal complex). The purity and elemental distribution of the ligand and ligand-metal complex were checked by EDX analysis and EDX mapping, and the results confirmed the presence of copper ions in the complex.

DFT method was carried out to further investigate the conformational properties and stabilities of the tautomeric forms of 3-HNHBH before and after complexation. Although the tautomeric forms of the ligand seem to exhibit comparable stabilities, the enol form (enol-b) which is assumed prior to complexation with the metal ion was predicted from DFT calculations to be around 13 kcal mol$^{-1}$ less stable with respect to the most stable keto configuration, as depicted in FIG. 5A. The transition states involving proton transfer from the hydrazonic nitrogen to the carbonyl oxygen to form enol-a lies significantly high (about 70 kcal mol$^{-1}$) on the potential energy scan. The relative stability suggests that keto to enol-a tautomerization is more likely to take place through an inter-rather than intra-molecular proton-transfer pathway. To facilitate the complexation of 3-HNHBH with the metal ion, the calculated TS2 corresponding to the conformational interchange from enol-a to enol-b is predicted to be located at a moderate height of 11 kcal mol$^{-1}$. The energy profile depicted in FIG. 5A is in agreement with the spectroscopic observations and the previous literature reports on the structural and conformational nature of hydrazone-based ligands. See Angelusiu et al; and Gup et al. (described above). Moreover, stable configurations of M(3-HNHBH)$_2^{2+}$ complexes (M=Cu, Ni or Zn) were successfully determined at the B3LYP/6-311+G(d) level of theory and shown in FIG. 5B. It can be noticed that Zn and Cu ions adopt a seesaw coordination environment with the ligand compared to a square planar configuration for the Ni counterpart. Furthermore, the bond distance of Cu—O (1.884 Å) was predicted to be shorter than those of Zn—O (2.097 Å) and Ni—O (2.237 Å), indicating a more pronounced coulombic interaction in the case of the copper ion complex which further explains the high sensitivity of the ligand towards Cu(ii) ions.

Similar computations are applicable to other divalent and multivalent ions of Periodic Table, taking into consideration the orbital structure of the ion, orbital overlap, strain introduced by binding of the ion of the defined size, the tautomeric equilibrium under the conditions compatible with ion's charge value. The Example below is applicable to any Cu(II)-Me pair, where Me is a potential interferent and is not limited to Cu(II)-Zn(II), Cu(II)-Ni(II) pairs exclusively.

Example 3: Specific Factors Determining Cu(II)-Me Selectivity. The Effect of Metal Interference Interference solutions containing Ni, Zn, and Cu ions were prepared each at a concentration of 2×10$^{-3}$ M and used for colorimetric titrations with 3-HBHBH ligand. When treated with a solution of Ni(ii) ions, a solution of Cu(3-HNHBH)$_2^{2+}$ showed no change in color. However, when the Zn(ii) solution was added, a slight color change was observed. An inspection of the UV-Vis spectrum of the ligand in the presence of the interference solutions (FIG. 6) showed that the absorption band around 350 nm was gradually decreasing. When the solution was spiked with Cu(OAc)$_2$ in THF, however, it showed a quick response to copper implying the selectivity of 3-HNHBH ligand towards copper(ii) ions in the presence of other metal ions. To provide a rational understanding of the nature of 3-HNHBH ligand interaction towards Cu, Ni and Zn metal ions, further investigation at the atomistic level was carried out by calculating metal-ligand binding energies, structural parameters of the optimized complexes and frontier molecular orbitals. Geometrical aspects listed in Table 1 for the three complexes revealed that both Cu and Zn ions tend to adopt a seesaw coordination environment with the nitrogen and oxygen-binding sites of the ligand, unlike the Ni ion which undergoes a square planar coordination. The DFT search for the minimum form of the Ni complex showed an appreciable steric repulsion between the two ligand molecules coordinated to the metal ion center, resulting in the least stable binding among the three metal ions. While the seesaw configuration has less experimental evidence in coordinated compounds of zinc and copper, it is thought to avail the more stable binding state with the ligand compared to the square planar Ni(3-HNHBH)$_2^{2+}$ metal complex (Table 1). See J. A. Bellow, D. Fang, N. Kovacevic, P. D. Martin, J. Shearer, G. A. Cisneros and S. Groysman, *Chem.-Eur. J.*, 2013, 19, 12225-12228; S. Fox, R. T. Stibrany, J. A. Potenza, S. Knapp and H. J. Schugar, *Inorg. Chem.*, 2000, 39, 4950-4961; L. Yang, D. R. Powell and R. P. Houser, *Dalton Trans.*, 2007, 955-964, DOI: 10.1039/b617136b; and T. Chu, L. Belding, P. K. Poddutoori, A. van der Est, T. Dudding, I. Korobkov and G. I. Nikonov, *Dalton Trans.*, 2016, 45, 13440-13448, each incorporated herein by reference in their entirety. Moreover, while the complexation with Zn(ii) ions was predicted to exhibit a relatively higher binding affinity followed by Cu then Ni, careful inspection of the calculated geometrical parameters and the qualitative overview of the structure (FIG. 5B) revealed that Cu ion suits a seesaw coordination environment with 3-HNHBH more conveniently than the Zn analog. The Cu(3-HNHBH)$_2^{2+}$ complex exercises the least deviation from the ideal seesaw arrangement and hence is more feasible of forming a stable complex with the ligand (Table 1). This agrees with the results from the preliminary studies presented in FIG. 1 where the ligand exhibited the most intense color change when added to a solution of Cu(OAc)$_2$. Despite having a relatively higher affinity towards Zn(ii) which is explained by the competitiveness in interference between these two metals, the ligand was found to be way more selective to Cu(ii) ions whose complex with the ligand results with smaller bond distances and closer angles to the ideal seesaw arrangement in comparison with the zinc counterpart. Furthermore, the frontier orbital distribution of 3-HNHBH ligand before and after complexation was computed and shown in FIG. 7. The charge transfer behavior of any two reacting molecules is a function of the spatial orientation of their frontier orbitals and the energy gap maintained as a result of their interaction. The molecular orbital interaction map shows that the ligand's HOMO-LUMO orbitals were fairly delocalized across the molecule, and the electron density located around the hydrazonic nitrogen atoms predicts a more likely binding site present for the metal ion. Upon the formation of the complex with the metal ions there was a corresponding decrease in energy. The Cu(ii) ion complex exhibits the least decrease in the energy gap among the three metal ions, which is further indicative of the higher stability of the complex formed with Cu(ii) ions relative to the other two metal ions. The relative selectivity of 3-HNHBH towards Cu(ii) compared to other metal ions could be attributed to its size that facilities the less usual seesaw coordination sphere with the least relative tilting as a result of binding to the ligand.

TABLE 1

Selected structural parameters and binding energies of metal ion complexes as calculated at the B3LYP/6-311 + G(d) level of theory

| | Cu (3-HNHBH)$_2^{2+}$ | Zn (3-HNHBH)$_2^{2+}$ | Ni (3-HNHBH)$_2^{2+}$ |
|---|---|---|---|
| Bond length (Å) | | | |
| M-O | 1.884 | 2.097 | 2.237 |
| M-N | 2.798 | 2.865 | 2.899 |
| M-O' | 1.889 | 1.979 | 1.963 |
| M-N' | 2.798 | 2.873 | 2.924 |
| Bond angle (deg.) | | | |
| N-M-N' | 170.11 | 156.29 | 177.05 |
| O-M-O' | 104.71 | 109.47 | 170.56 |
| N-M-O | 72.52 | 77.97 | 80.74 |
| N'-M-O' | 75.95 | 78.54 | 80.77 |
| Binding energy (kcal mol$^{-1}$) | | | |
| | −196 | −226 | −169 |

Example 4: Factors Determining Cu(II)-Me Selectivity. The Effect of Solvents

The effects of polar solvents acetonitrile (ACN) and tetrahydrofuran (THF) on the sensitivity and selectivity of 3-HNHBH towards Cu(ii) ions were investigated. Preparation of solutions of metal precursors was carried out in 50% (v/v) THF mixed aqueous solutions. The solution was used to dilute the 3-HNHBH ligand at 25% (w/v), 50% (w/v) and 75% (w/v), and tests were carried out on the ligand and metal precursors in mixed aqueous solutions following similar procedure in the preliminary studies. Selectivity of the ligand towards Cu(ii) ions increased as a very intense yellowish solution was formed upon the addition of ACN. UV-Vis spectrum of the ligand-metal complex in acetonitrile is presented in FIG. 6. The spectrum appears similar to that of the complex in pure THF (FIG. 4). Notably, the isosbestic points remained at 315 and 383 nm, but the absorption maxima of the complex shifted slightly from 324 to 330 nm and from 383 to 376 nm. Such observed small hypsochromic shift could be attributed to the addition of ACN which is more polar than THF. The ligand-metal complex in THF/ACN was also observed to absorb more strongly in the region of 420 to 520 nm than the complex in pure THF. This is a result of the tendency of ACN solvent to stabilize the ligand's non-bonding orbitals via hydrogen bonding, and this ultimately increases the amount of energy needed to excite an electron from a non-bonding orbital.

Example 5: Factors Determining Cu(II)-Me Selectivity. The Effect of pH

Studying the effect of the change in pH of the medium determines the sensitivity of 3-HNHBH towards Cu(ii) ions.

The ligand has been proposed to bind to the metal ion through free electron pairs present on its oxygen and nitrogen atoms. While in the presence of a base the nitrogen and oxygen atoms may undergo deprotonation to enhance the binding ability of the ligand to the metal ion, the addition of an acid, on the other hand, tends to protonate the nitrogen and oxygen atoms and thus interferes with the formation of the complex. Such an acid-base protonation-deprotonation process facilitates-defacilitates the regeneration of the organic ligand. In order to investigate this, aqueous solutions of $2 \times 10^{-4}$ M 3-HNHBH ligand (0.5 mL) and $2 \times 10^{-3}$ M metal salts (10 µL) were mixed in glass vials, and 1-10 µL aqueous 0.5 M HCl solution was added followed by aqueous 0.5 M NaOH solution, and vice versa. The reason for the choice of NaOH as the investigative base for pH effect was because a solution of the ligand did not produce a color change when NaCl was added. A distinct color change without a noted change in pH was observed when a few drops of the acid or base were added to the solution of the ligand. In addition, the color change was observed to be independent of the composition of the mixed aqueous solutions. An addition of the base to a mixed aqueous solution of the ligand and metal precursors increased the selectivity of 3-HNHBH towards Cu(ii) as shown in Table 2. Moreover, adding a few drops of a 0.5 M HCl solution to a mixed aqueous solution of the ligand and metal precursors other than Cu(ii) ended up with colorless solutions, while a subsequent introduction of Cu(ii) ions to the same solution turned it pale-greenish yellow, confirming the preference of 3-HNHBH towards Cu(ii) ions.

in the basic medium, while the acidic medium is shown to facilitate the regeneration of the ligand to its free form.

To determine the sensitivity level of the ligand to varying concentrations of copper ions, colorimetric titration was carried out by adding 0.5 mL of the ligand solution in THF ($2 \times 10^{-4}$ M) to 2.5 mL THF in a quartz cell and scanned from 200 to 700 nm. Then, the concentration of the ions was varied by the addition of 10 µL aliquots, and the UV-Vis spectra were recorded. A corresponding linear response was observed with a detection limit (S/N=3) of 0.34 µg $L^{-1}$.

The influence of acid or base additions can be further explained in terms of keto-enol tautomerism of 3-HNHBH ligand. Keto-enol tautomerization refers to a chemical equilibrium that exists between the two forms of the molecule; namely the keto form having a carbonyl group and the enol form having a pair of doubly bonded atoms adjacent to a hydroxyl group. Addition of a 0.5 M HCl solution protonates the enolic hydroxyl group releasing the metal ions from the ligand-metal complex, while the addition of 0.5 M NaOH solution improves the preference of the ligand for the metal ions. To further elucidate the effect of change in pH on the complexation of 3-HNHBH with metal ions, Mulliken atomic charge distribution on the atoms of the ligand were calculated. Atomic charges on prominent sites of the ligand where protonation may occur are summarized in Table 3. The atomic charge distribution is normally used to predict chemical reactivities of a given molecule under various pH conditions. It provides useful insights on the electronic

TABLE 2

Description of color changes when aqueous solutions of NaOH and HCl are added to 3-HNHBH solutions of metal salts

| | Metal salt | Ni(acac)$_2$ | Cu(OAc)$_2$ | Zn(OAc)$_2$ |
|---|---|---|---|---|
| | Initial solution color | Pale green-yellow | Pale green-yellow | Very, very pale green-yellow |
| Set 1 | +1 µL NaOH | Greenish-yellow | Bright-yellow | Greenish-yellow |
| | +1 µL HCl | Colourless | Pale green-yellow | Colourless |
| Set 2 | +1 µL HCl | Colourless | Colourless | Colourless |
| | +2 µL NaOH | Greenish-yellow | Pale green-yellow | Greenish-yellow |

Further, the selectivity of 3-HNHBH towards copper(ii) ions in the presence of EDTA was investigated by preparing 50% THF mixed aqueous solutions of tetrasodium ethylenediaminetetraacetate (Na$_4$-EDTA) at different concentrations. 50% THF mixed aqueous solutions of $2 \times 10^{-3}$ M metal salts, Ni(acac)$_2$, Zn(OAc)$_2$, and Cu(OAc)$_2$ were prepared and introduced in 10 µL aliquots to a 0.5 mL Na$_4$-EDTA solution ($2 \times 10^{-4}$ M) in a glass vial, and color changes were noted. Mixed aqueous solutions of $2 \times 10^{-4}$ M 3-HNHBH ligand and 10 µL of $2 \times 10^{-3}$ M metal salts in a glass vial were mixed with 1-10 µL, of $2 \times 10^{-2}$ M and $2 \times 10^{-4}$ M Na$_4$-EDTA solutions, respectively. At acidic conditions, a colorless solution was observed, whereas at basic conditions a yellowish color was developed; similar to that which contains no EDTA. At basic conditions, the presence of EDTA alone led to the formation of a yellowish color in the presence of 3-HNHBH. This indicates that at basic conditions the ligand competes with EDTA in coordinating with Cu(ii) ions, with the metal ions having more preference for the ligand. In the acidic condition, however, the ligand is no longer bound to the copper ions which confirm the ligand decomplexation being a means to regenerate the ligand from the complex. It is concluded from all the above observations that the selectivity of 3-HNHBH towards Cu(ii) ions could be enhanced features of the molecule, and from this it is possible to predict bonding, anti-bonding or non-bonding features of the molecule. See M.-J. Lee and B.-D. Lee, Tetrahedron Lett., 2010, 51, 3782-3785, incorporated herein by reference in its entirety. The calculated atomic charges for the 3-HNHBH complex were remarkably negative on the oxygen atoms of the carbonyl group and hydroxyl group para to carbonyl (O and $O_h$) as shown in Table 3. This correlates with experimental results in which the addition of a strong acid even at small quantities results in discoloration of the complex as a result of fast protonation of the hydroxyl and carbonyl oxygen atoms.

TABLE 3

Calculated Mulliken Atomic charges (e$^-$) on selected atoms of the 3-HNHBH ligand

| Atom | Charge |
|---|---|
| O | −0.697 |
| N | −0.327 |
| $O_a$ | −0.601 |
| $O_h$ | −0.641 |

The invention claimed is:

1. A method of detecting the presence of copper (ID) ions in an aqueous sample, comprising:
    measuring an absorbance of the aqueous sample,
    contacting a compound having structure (II) with the aqueous sample to form a complexation mixture; then

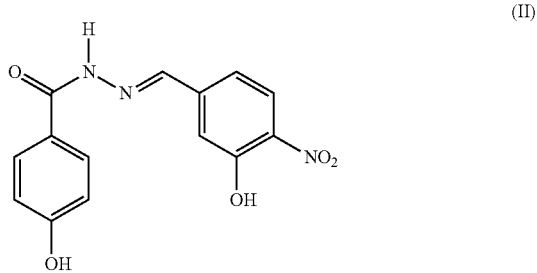 [SMILES: O=C(N/N=C/c1ccc([N+](=O)[O-])c(O)c1)c1ccc(O)cc1]
(II)

determining a difference in absorption at a wavelength in the range of 250-520 nm between the aqueous sample and the complexation mixture and,
detecting the presence of copper (II) ions in an aqueous sample based on the difference in absorption.

2. The method of claim 1, wherein a detection threshold for the copper (II) ion is below 5 nM.

3. The method of claim 1, wherein a detection threshold for the copper (II) ion is below 5 nM and the copper (II) ion is detected in the presence of d-, f- and g-element interferents at a [$Cu^{2+}$]/[interferents] ratio of 1:1 or lower.

4. The method of claim 1, wherein selectivity for the copper (II) ion is optimized by regulating the pH during the contacting and/or by modifying a solvent composition during the contacting.

5. The method of claim 1, wherein the aqueous sample is at least one selected from the group consisting of a geological survey sample, an artesian water sample, a drinkable water supply sample, a waste flow sample and a factory recycle sample.

6. The method of claim 1, wherein the compound of formula (II) is 3-HNHBH.

* * * * *